United States Patent
Fong et al.

(10) Patent No.: US 6,878,520 B1
(45) Date of Patent: Apr. 12, 2005

(54) C-TERMINAL REGION OF AGOUTI-RELATED TRANSCRIPT (ART) PROTEIN

(75) Inventors: Tung Ming Fong, Somerset, NJ (US); Leonardus H. T. Van Der Ploeg, Scotch Plains, NJ (US); Michael R. Tota, Middletown, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/581,894

(22) PCT Filed: Dec. 11, 1998

(86) PCT No.: PCT/US98/26457

§ 371 (c)(1),
(2), (4) Date: Aug. 21, 2000

(87) PCT Pub. No.: WO99/31508

PCT Pub. Date: Jun. 24, 1999

Related U.S. Application Data

(60) Provisional application No. 60/069,747, filed on Dec. 16, 1997.

(51) Int. Cl.[7] ................ C07K 19/00; C12N 15/62
(52) U.S. Cl. ................ 435/7.1; 435/7.2; 530/300; 530/350; 536/23.4; 436/501
(58) Field of Search ................ 530/300, 350; 536/23.4; 435/7.1, 7.2; 436/501

(56) References Cited

U.S. PATENT DOCUMENTS 5,766,877 A * 6/1998 Stark et al.
6,060,589 A * 5/2000 Stark et al.
6,203,995 B1 * 3/2001 Stark

FOREIGN PATENT DOCUMENTS

WO    WO 97/43412    * 11/1997
WO    WO 97/47316      12/1997

OTHER PUBLICATIONS

Willard et al., Biochemistry, vol. 34, No. 38, pp 12341–12346 (1995).
Perry et al., Genetics, vol. 140, No. 1, pp 267–27, (1995).
Bodi et al., Tetrahedron Letters, vol. 38, No. 18, pp. 3293–3296 (1997).
Haskell–Luevano et al., Journal of Medicinal Chemists, vol. 40, No. 14, pp. 2133–2139 (1997).
Ollmann et al., Science, vol. 278, pp. 135–138 (1997).
Shutter, et al. 1997; Genes & Development 11:593–602.
Fong, et al.; Biochem, Biophys, Res. Comm. 237:629–631.
Mountjoy et al. 1994 Mol. Endo Crinol 8:1298–1308.
Bray; 1997 Nutr. Rev. 45:33–43.
Huszar, et al. 1997 Cell 88:131–141.
Stark, 1996 EMBJ 5:1995–2002 (1986).
Kwon 94 PNAS 91:9760–64.

* cited by examiner

Primary Examiner—Elizabeth Kemmerer
(74) Attorney, Agent, or Firm—J. David Reilly; Joanne M. Giesser

(57) ABSTRACT

Novel polypeptides derived from the C-terminal region of the human and mouse agouti related transcript (ART) proteins are provided. Also provided are DNA sequences encoding the novel C-terminal polypeptides. The novel C-terminal polypeptides can be used to inhibit the binding of melanocyte stimulating hormones to melanocortin receptors. Methods of identifying inhibitors of the binding of ART protein to melanocortin receptors are also provided.

16 Claims, 3 Drawing Sheets

SEQUENCE LISTING

```
<160> NUMBER OF SEQ ID NOS: 24

<210> SEQ ID NO 1
<211> LENGTH: 118
<212> TYPE: PRT
<213> ORGANISM: Human

<400> SEQUENCE: 1

Met Asn Ile Phe Tyr Ile Phe Leu Phe Leu Leu Ser Phe Val Gln Gly
 1               5                  10                  15

Leu Glu His Thr His Arg Arg Gly Ser Leu Val Lys Arg Ser Ser Leu
            20                  25                  30

Gln Asp Arg Glu Pro Arg Ser Ser Arg Arg Cys Val Arg Leu His Glu
        35                  40                  45

Ser Cys Leu Gly Gln Gln Val Pro Cys Cys Asp Pro Cys Ala Thr Cys
    50                  55                  60

Tyr Cys Arg Phe Phe Asn Ala Phe Cys Tyr Cys Arg Lys Leu Gly Thr
65                  70                  75                  80

Ala Met Asn Pro Cys Ser Arg Thr Leu Val Pro Arg Gly Ser Glu Gln
                85                  90                  95

Lys Leu Ile Ser Glu Glu Asp Leu Asn Leu Arg Arg Ala Ser Leu Gly
            100                 105                 110

His His His His His His
        115

<210> SEQ ID NO 2
<211> LENGTH: 120
<212> TYPE: PRT
<213> ORGANISM: Human

<400> SEQUENCE: 2

Met Leu Thr Ala Ala Leu Leu Ser Cys Ala Leu Leu Leu Ala Leu Pro
 1               5                  10                  15

Ala Thr Arg Gly Ala Gln Met Gly Leu Ala Leu Gln Asp Arg Glu Pro
            20                  25                  30

Arg Ser Ser Arg Arg Cys Val Arg Leu His Glu Ser Cys Leu Gly Gln
        35                  40                  45

Gln Val Pro Cys Cys Asp Pro Cys Ala Thr Cys Tyr Cys Arg Phe Phe
    50                  55                  60

Asn Ala Phe Cys Tyr Cys Arg Lys Leu Gly Thr Ala Met Asn Pro Cys
65                  70                  75                  80

Ser Arg Thr Leu Val Pro Arg Gly Ser Gly Ser Glu Leu Gly Thr Lys
                85                  90                  95
```

```
Leu Gly Pro Glu Gln Lys Leu Ile Ser Glu Glu Asp Leu Asn Ser Ala
            100                 105                 110

Val Asp His His His His His His
            115                 120

<210> SEQ ID NO 3
<211> LENGTH: 121
<212> TYPE: PRT
<213> ORGANISM: Human

<400> SEQUENCE: 3

Met Leu Thr Ala Ala Leu Leu Ser Cys Ala Leu Leu Ala Leu Pro
  1               5                  10                  15

Ala Thr Arg Gly Ala Gln Met Gly Leu Ala Leu Gln Asp Arg Glu Pro
             20                  25                  30

Arg Ser Ser Arg Arg Cys Val Arg Leu His Glu Ser Cys Leu Gly Gln
             35                  40                  45

Gln Val Pro Cys Cys Asp Pro Cys Ala Thr Cys Tyr Cys Arg Phe Phe
         50                  55                  60

Asn Ala Phe Cys Tyr Cys Arg Lys Leu Gly Thr Ala Met Asn Pro Cys
 65                  70                  75                  80

Ser Arg Thr Leu Val Pro Arg Gly Ser Gly Ser Leu Arg Arg Ala Ser
                 85                  90                  95

Leu Gly Lys Leu Glu Gln Lys Leu Ile Ser Glu Glu Asp Leu Asn Ser
            100                 105                 110

Ala Val Asp His His His His His His
            115                 120

<210> SEQ ID NO 4
<211> LENGTH: 654
<212> TYPE: PRT
<213> ORGANISM: Human

<400> SEQUENCE: 4

Met Leu Thr Ala Ala Leu Leu Ser Cys Ala Leu Leu Ala Leu Pro
  1               5                  10                  15

Ala Thr Arg Gly Ala Gln Met Gly Leu Ala Pro Met Glu Gly Ile Arg
             20                  25                  30

Arg Pro Asp Gln Ala Leu Leu Pro Glu Leu Pro Gly Leu Gly Leu Arg
             35                  40                  45

Ala Pro Leu Lys Lys Thr Asn Ala Glu Gln Ala Glu Glu Asp Leu Leu
         50                  55                  60

Gln Glu Ala Gln Ala Leu Ala Glu Val Leu Asp Leu Gln Asp Arg Glu
 65                  70                  75                  80

Pro Arg Ser Ser Arg Arg Cys Val Arg Leu His Glu Ser Cys Leu Gly
                 85                  90                  95

Gln Gln Val Pro Cys Cys Asp Pro Cys Ala Thr Cys Tyr Cys Arg Phe
            100                 105                 110

Phe Asn Ala Phe Cys Tyr Cys Arg Lys Leu Gly Thr Ala Met Asn Pro
            115                 120                 125

Cys Ser Arg Thr Leu Val Pro Arg Gly Ser Gly Ser Ile Ile Pro Val
            130                 135                 140

Glu Glu Glu Asn Pro Asp Phe Trp Asn Arg Gln Ala Ala Glu Ala Leu
145                 150                 155                 160

Gly Ala Ala Lys Lys Leu Gln Pro Ala Gln Thr Ala Ala Lys Asn Leu
                165                 170                 175
```

-continued

```
Ile Ile Phe Leu Gly Asp Gly Met Gly Val Ser Thr Val Thr Ala Ala
            180             185             190

Arg Ile Leu Lys Gly Gln Lys Lys Asp Lys Leu Gly Pro Glu Thr Phe
        195             200             205

Leu Ala Met Asp Arg Phe Pro Tyr Val Ala Leu Ser Lys Thr Tyr Ser
        210             215             220

Val Asp Lys His Val Pro Asp Ser Gly Ala Thr Ala Thr Ala Tyr Leu
225             230             235             240

Cys Gly Val Lys Gly Asn Phe Gln Thr Ile Gly Leu Ser Ala Ala Ala
            245             250             255

Arg Phe Asn Gln Cys Asn Thr Thr Arg Gly Asn Glu Val Ile Ser Val
            260             265             270

Met Asn Arg Ala Lys Lys Ala Gly Lys Ser Val Gly Val Val Thr Thr
        275             280             285

Thr Arg Val Gln His Ala Ser Pro Ala Gly Ala Tyr Ala His Thr Val
        290             295             300

Asn Arg Asn Trp Tyr Ser Asp Ala Asp Val Pro Ala Ser Ala Arg Gln
305             310             315             320

Glu Gly Cys Gln Asp Ile Ala Thr Gln Leu Ile Ser Asn Met Asp Ile
            325             330             335

Asp Val Ile Leu Gly Gly Gly Arg Lys Tyr Met Phe Pro Met Gly Thr
            340             345             350

Pro Asp Pro Glu Tyr Pro Asp Asp Tyr Ser Gln Gly Gly Thr Arg Leu
        355             360             365

Asp Gly Lys Asn Leu Val Gln Glu Trp Leu Ala Lys His Gln Gly Ala
        370             375             380

Arg Tyr Val Trp Asn Arg Thr Glu Leu Met Gln Ala Ser Leu Asp Pro
385             390             395             400

Ser Val Thr His Leu Met Gly Leu Phe Glu Pro Gly Asp Met Lys Tyr
            405             410             415

Glu Ile His Arg Asp Ser Thr Leu Asp Pro Ser Leu Met Glu Met Thr
            420             425             430

Glu Ala Ala Leu Arg Leu Leu Ser Arg Asn Pro Arg Gly Phe Phe Leu
        435             440             445

Phe Val Glu Gly Gly Arg Ile Asp His Gly His His Glu Ser Arg Ala
450             455             460

Tyr Arg Ala Leu Thr Glu Thr Ile Met Phe Asp Asp Ala Ile Glu Arg
465             470             475             480

Ala Gly Gln Leu Thr Ser Glu Asp Thr Leu Ser Leu Val Thr Ala
            485             490             495

Asp His Ser His Val Phe Ser Phe Gly Gly Tyr Pro Leu Arg Gly Ser
            500             505             510

Ser Ile Phe Gly Leu Ala Pro Gly Lys Ala Arg Asp Arg Lys Ala Tyr
        515             520             525

Thr Val Leu Leu Tyr Gly Asn Gly Pro Gly Tyr Val Leu Lys Asp Gly
        530             535             540

Ala Arg Pro Asp Val Thr Glu Ser Glu Ser Gly Ser Pro Glu Tyr Arg
545             550             555             560

Gln Gln Ser Ala Val Pro Leu Asp Gly Glu Thr His Ala Gly Glu Asp
            565             570             575

Val Ala Val Phe Ala Arg Gly Pro Gln Ala His Leu Val His Gly Val
            580             585             590

Gln Glu Gln Thr Phe Ile Ala His Val Met Ala Phe Ala Ala Cys Leu
```

```
                    595                 600                 605
Glu Pro Tyr Thr Ala Cys Asp Leu Ala Pro Ser Ala Gly Thr Thr Asp
            610                 615                 620

Ala Ala His Pro Gly Lys Leu Gly Pro Glu Gln Lys Leu Ile Ser Glu
625                 630                 635                 640

Glu Asp Leu Asn Ser Ala Val Asp His His His His His
                645                 650

<210> SEQ ID NO 5
<211> LENGTH: 715
<212> TYPE: PRT
<213> ORGANISM: Human

<400> SEQUENCE: 5

Met Leu Thr Ala Ala Leu Leu Ser Cys Ala Leu Leu Ala Leu Pro
 1               5                  10                  15

Ala Thr Arg Gly Ala Gln Met Gly Leu Ala Pro Met Glu Gly Ile Arg
                20                  25                  30

Arg Pro Asp Gln Ala Leu Leu Pro Glu Leu Pro Gly Leu Gly Leu Arg
                35                  40                  45

Ala Pro Leu Lys Lys Thr Asn Ala Glu Gln Ala Glu Glu Asp Leu Leu
50                  55                  60

Gln Glu Ala Gln Ala Leu Ala Glu Val Leu Asp Leu Gln Asp Arg Glu
65                  70                  75                  80

Pro Arg Ser Ser Arg Arg Cys Val Arg Leu His Glu Ser Cys Leu Gly
                85                  90                  95

Gln Gln Val Pro Cys Cys Asp Pro Cys Ala Thr Cys Tyr Cys Arg Phe
                100                 105                 110

Phe Asn Ala Phe Cys Tyr Cys Arg Lys Leu Gly Thr Ala Met Asn Pro
            115                 120                 125

Cys Ser Arg Thr Leu Val Pro Arg Gly Ser Gly Ser Met Ser Ile Glu
    130                 135                 140

Asn Asn Ile Leu Ile Gly Pro Pro Pro Tyr Tyr Pro Leu Glu Glu Gly
145                 150                 155                 160

Thr Ala Gly Glu Gln Leu His Arg Ala Ile Ser Arg Tyr Ala Ala Val
                165                 170                 175

Pro Gly Thr Leu Ala Tyr Thr Asp Val His Thr Glu Leu Glu Val Thr
                180                 185                 190

Tyr Lys Glu Phe Leu Asp Val Thr Cys Arg Leu Ala Glu Ala Met Lys
            195                 200                 205

Asn Tyr Gly Leu Gly Leu Gln His Thr Ile Ser Val Cys Ser Glu Asn
    210                 215                 220

Cys Val Gln Phe Phe Met Pro Ile Cys Ala Ala Leu Tyr Val Gly Val
225                 230                 235                 240

Ala Thr Ala Pro Thr Asn Asp Ile Tyr Asn Glu Arg Glu Leu Tyr Asn
                245                 250                 255

Ser Leu Ser Ile Ser Gln Pro Thr Val Val Phe Thr Ser Arg Asn Ser
                260                 265                 270

Leu Gln Lys Ile Leu Gly Val Gln Ser Arg Leu Pro Ile Ile Lys Lys
            275                 280                 285

Ile Ile Ile Leu Asp Gly Lys Lys Asp Tyr Leu Gly Tyr Gln Ser Met
    290                 295                 300

Gln Ser Phe Met Lys Glu His Val Pro Ala Asn Phe Asn Val Ser Ala
305                 310                 315                 320
```

```
Phe Lys Pro Leu Ser Phe Asp Leu Asp Arg Val Ala Cys Ile Met Asn
            325                 330                 335

Ser Ser Gly Ser Thr Gly Leu Pro Lys Gly Val Pro Ile Ser His Arg
            340                 345                 350

Asn Thr Ile Tyr Arg Phe Ser His Cys Arg Asp Pro Val Phe Gly Asn
            355                 360                 365

Gln Ile Ile Pro Asp Thr Thr Ile Leu Cys Ala Val Pro Phe His His
    370                 375                 380

Ala Phe Gly Thr Phe Thr Asn Leu Gly Tyr Leu Ile Cys Gly Phe His
385                 390                 395                 400

Val Val Leu Met Tyr Arg Phe Asn Glu His Leu Phe Leu Gln Thr Leu
                405                 410                 415

Gln Asp Tyr Lys Cys Gln Ser Ala Leu Leu Val Pro Thr Val Leu Ala
            420                 425                 430

Phe Leu Ala Lys Asn Pro Leu Val Asp Lys Tyr Asp Leu Ser Asn Leu
            435                 440                 445

His Glu Ile Ala Ser Gly Gly Ala Pro Leu Ser Lys Glu Ile Ser Glu
    450                 455                 460

Ile Ala Ala Lys Arg Phe Lys Leu Pro Gly Ile Arg Gln Gly Tyr Gly
465                 470                 475                 480

Leu Thr Glu Thr Thr Cys Ala Ile Val Ile Thr Ala Glu Gly Glu Phe
                485                 490                 495

Lys Leu Gly Ala Val Gly Lys Val Val Pro Phe Tyr Ser Leu Lys Val
            500                 505                 510

Leu Asp Leu Asn Thr Gly Lys Lys Leu Gly Pro Asn Glu Arg Gly Glu
    515                 520                 525

Ile Cys Phe Lys Gly Pro Met Ile Met Lys Gly Tyr Ile Asn Asn Pro
530                 535                 540

Glu Ala Thr Arg Glu Leu Ile Asp Glu Glu Gly Trp Ile His Ser Gly
545                 550                 555                 560

Asp Ile Gly Tyr Phe Asp Glu Asp Gly His Val Tyr Ile Val Asp Arg
                565                 570                 575

Leu Lys Ser Leu Ile Lys Tyr Lys Gly Tyr Gln Val Pro Pro Ala Glu
            580                 585                 590

Leu Glu Ala Leu Leu Leu Gln His Pro Phe Ile Glu Asp Ala Gly Val
    595                 600                 605

Ala Gly Val Pro Asp Glu Val Ala Gly Asp Leu Pro Gly Ala Val Val
610                 615                 620

Val Leu Lys Glu Gly Lys Ser Ile Thr Glu Lys Glu Ile Gln Asp Tyr
625                 630                 635                 640

Val Ala Gly Gln Val Thr Ser Ser Lys Lys Leu Arg Gly Gly Val Glu
                645                 650                 655

Phe Val Lys Glu Val Pro Lys Gly Phe Thr Gly Lys Ile Asp Thr Arg
            660                 665                 670

Lys Ile Lys Glu Ile Leu Ile Lys Ala Gln Lys Gly Lys Ser Lys Ser
    675                 680                 685

Lys Ala Lys Leu Gly Pro Glu Gln Lys Leu Ile Ser Glu Glu Asp Leu
690                 695                 700

Asn Ser Ala Val Asp His His His His His
705                 710                 715

<210> SEQ ID NO 6
<211> LENGTH: 83
<212> TYPE: PRT
```

-continued

<213> ORGANISM: Human

<400> SEQUENCE: 6

Met Leu Thr Ala Ala Leu Leu Ser Cys Ala Leu Leu Ala Leu Pro
1               5                   10                  15

Ala Thr Arg Gly Ala Gln Met Gly Leu Ala Leu Gln Asp Arg Glu Pro
            20                  25                  30

Arg Ser Ser Arg Arg Cys Val Arg Leu His Glu Ser Cys Leu Gly Gln
            35                  40                  45

Gln Val Pro Cys Cys Asp Pro Cys Ala Thr Cys Tyr Cys Arg Phe Phe
        50                  55                  60

Asn Ala Phe Cys Tyr Cys Arg Lys Leu Gly Thr Ala Met Asn Pro Cys
65                  70                  75                  80

Ser Arg Thr

<210> SEQ ID NO 7
<211> LENGTH: 57
<212> TYPE: PRT
<213> ORGANISM: Human

<400> SEQUENCE: 7

Leu Gln Asp Arg Glu Pro Arg Ser Ser Arg Arg Cys Val Arg Leu His
1               5                   10                  15

Glu Ser Cys Leu Gly Gln Gln Val Pro Cys Cys Asp Pro Cys Ala Thr
            20                  25                  30

Cys Tyr Cys Arg Phe Phe Asn Ala Phe Cys Tyr Cys Arg Lys Leu Gly
        35                  40                  45

Thr Ala Met Asn Pro Cys Ser Arg Thr
        50                  55

<210> SEQ ID NO 8
<211> LENGTH: 83
<212> TYPE: PRT
<213> ORGANISM: Mouse

<400> SEQUENCE: 8

Met Leu Thr Ala Met Leu Leu Ser Cys Val Leu Leu Ala Leu Pro
1               5                   10                  15

Pro Thr Leu Gly Val Gln Met Gly Val Ala Pro Gln Asn Arg Glu Ser
            20                  25                  30

Arg Ser Pro Arg Arg Cys Val Arg Leu His Glu Ser Cys Leu Gly Gln
            35                  40                  45

Gln Val Pro Cys Cys Asp Pro Cys Ala Thr Cys Tyr Cys Arg Phe Phe
        50                  55                  60

Asn Ala Phe Cys Tyr Cys Arg Lys Leu Gly Thr Ala Met Asn Leu Cys
65                  70                  75                  80

Ser Arg Thr

<210> SEQ ID NO 9
<211> LENGTH: 57
<212> TYPE: PRT
<213> ORGANISM: Mouse

<400> SEQUENCE: 9

Pro Gln Asn Arg Glu Ser Arg Ser Pro Arg Arg Cys Val Arg Leu His
1               5                   10                  15

Glu Ser Cys Leu Gly Gln Gln Val Pro Cys Cys Asp Pro Cys Ala Thr
            20                  25                  30

```
Cys Tyr Cys Arg Phe Phe Asn Ala Phe Cys Tyr Cys Arg Lys Leu Gly
            35                  40                  45

Thr Ala Met Asn Leu Cys Ser Arg Thr
 50                  55
```

<210> SEQ ID NO 10
<211> LENGTH: 118
<212> TYPE: PRT
<213> ORGANISM: Mouse

<400> SEQUENCE: 10

```
Met Asn Ile Phe Tyr Ile Phe Leu Phe Leu Ser Phe Val Gln Gly
 1               5                  10                  15

Leu Glu His Thr His Arg Arg Gly Ser Leu Val Lys Arg Ser Ser Pro
                20                  25                  30

Gln Asn Arg Glu Ser Arg Ser Pro Arg Arg Cys Val Arg Leu His Glu
            35                  40                  45

Ser Cys Leu Gly Gln Gln Val Pro Cys Cys Asp Pro Cys Ala Thr Cys
 50                  55                  60

Tyr Cys Arg Phe Phe Asn Ala Phe Cys Tyr Cys Arg Lys Leu Gly Thr
 65                  70                  75                  80

Ala Met Asn Leu Cys Ser Arg Thr Leu Val Pro Arg Gly Ser Glu Gln
                85                  90                  95

Lys Leu Ile Ser Glu Glu Asp Leu Asn Leu Arg Arg Ala Ser Leu Gly
                100                 105                 110

His His His His His His
            115
```

<210> SEQ ID NO 11
<211> LENGTH: 113
<212> TYPE: PRT
<213> ORGANISM: Mouse

<400> SEQUENCE: 11

```
Met Leu Thr Ala Met Leu Leu Ser Cys Val Leu Leu Ala Leu Pro
 1               5                  10                  15

Pro Thr Leu Gly Val Gln Met Gly Val Ala Pro Gln Asn Arg Glu Ser
                20                  25                  30

Arg Ser Pro Arg Arg Cys Val Arg Leu His Glu Ser Cys Leu Gly Gln
            35                  40                  45

Gln Val Pro Cys Cys Asp Pro Cys Ala Thr Cys Tyr Cys Arg Phe Phe
 50                  55                  60

Asn Ala Phe Cys Tyr Cys Arg Lys Leu Gly Thr Ala Met Asn Leu Cys
 65                  70                  75                  80

Ser Arg Thr Leu Val Pro Arg Gly Ser Glu Gln Lys Leu Ile Ser Glu
                85                  90                  95

Glu Asp Leu Asn Leu Arg Arg Ala Ser Leu Ser His His His His His
                100                 105                 110

His
```

<210> SEQ ID NO 12
<211> LENGTH: 117
<212> TYPE: PRT
<213> ORGANISM: Mouse

<400> SEQUENCE: 12

Met Leu Thr Ala Met Leu Leu Ser Cys Val Leu Leu Ala Leu Pro

-continued

```
             1               5                  10                 15
Pro Thr Leu Gly Val Gln Met Gly Val Ala Pro Gln Asn Arg Glu Ser
                20                  25                 30

Arg Ser Pro Arg Arg Cys Val Arg Leu His Glu Ser Cys Leu Gly Gln
            35                  40                 45

Gln Val Pro Cys Cys Asp Pro Cys Ala Thr Cys Tyr Cys Arg Phe Phe
        50                  55                 60

Asn Ala Phe Cys Tyr Cys Arg Lys Leu Gly Thr Ala Met Asn Leu Cys
65                  70                  75                 80

Ser Arg Thr Leu Val Pro Arg Gly Ser Gly Ser Leu Arg Arg Ala Ser
                85                  90                 95

Leu Gly Lys Leu Glu Gln Lys Leu Ile Ser Glu Glu Asp Leu Asn His
            100                 105                110

His His His His His
            115

<210> SEQ ID NO 13
<211> LENGTH: 620
<212> TYPE: PRT
<213> ORGANISM: Mouse

<400> SEQUENCE: 13

Met Leu Thr Ala Met Leu Leu Ser Cys Val Leu Leu Ala Leu Pro
1               5                  10                 15

Pro Thr Leu Gly Val Gln Met Gly Val Ala Pro Leu Lys Gly Ile Arg
                20                  25                 30

Arg Pro Asp Gln Ala Leu Phe Pro Glu Phe Pro Gly Leu Ser Leu Asn
            35                  40                 45

Gly Leu Lys Lys Thr Asn Ala Asp Arg Ala Glu Glu Val Leu Leu Gln
        50                  55                 60

Lys Ala Glu Ala Leu Ala Glu Val Leu Asp Pro Gln Asn Arg Glu Ser
65                  70                  75                 80

Arg Ser Pro Arg Arg Cys Val Arg Leu His Glu Ser Cys Leu Gly Gln
                85                  90                 95

Gln Val Pro Cys Cys Asp Pro Cys Ala Thr Cys Tyr Cys Arg Phe Phe
            100                 105                110

Asn Ala Phe Cys Tyr Cys Arg Lys Leu Gly Thr Ala Met Asn Leu Cys
        115                 120                125

Ser Arg Thr Ile Ile Pro Val Glu Glu Glu Asn Pro Asp Phe Trp Asn
    130                 135                 140

Arg Gln Ala Ala Glu Ala Leu Gly Ala Ala Lys Lys Leu Gln Pro Ala
145                 150                 155                160

Gln Thr Ala Ala Lys Asn Leu Ile Ile Phe Leu Gly Asp Gly Met Gly
                165                 170                175

Val Ser Thr Val Thr Ala Ala Arg Ile Leu Lys Gly Gln Lys Lys Asp
            180                 185                190

Lys Leu Gly Pro Glu Thr Phe Leu Ala Met Asp Arg Phe Pro Tyr Val
        195                 200                205

Ala Leu Ser Lys Thr Tyr Ser Val Asp Lys His Val Pro Asp Ser Gly
    210                 215                 220

Ala Thr Ala Thr Ala Tyr Leu Cys Gly Val Lys Gly Asn Phe Gln Thr
225                 230                 235                240

Ile Gly Leu Ser Ala Ala Ala Arg Phe Asn Gln Cys Asn Thr Thr Arg
                245                 250                255
```

```
Gly Asn Glu Val Ile Ser Val Met Asn Arg Ala Lys Lys Ala Gly Lys
            260                 265                 270

Ser Val Gly Val Val Thr Thr Thr Arg Val Gln His Ala Ser Pro Ala
        275                 280                 285

Gly Ala Tyr Ala His Thr Val Asn Arg Asn Trp Tyr Ser Asp Ala Asp
    290                 295                 300

Val Pro Ala Ser Ala Arg Gln Glu Gly Cys Gln Asp Ile Ala Thr Gln
305                 310                 315                 320

Leu Ile Ser Asn Met Asp Ile Asp Val Ile Leu Gly Gly Arg Lys
                325                 330                 335

Tyr Met Phe Pro Met Gly Thr Pro Asp Pro Glu Tyr Pro Asp Asp Tyr
            340                 345                 350

Ser Gln Gly Gly Thr Arg Leu Asp Gly Lys Asn Leu Val Gln Glu Trp
        355                 360                 365

Leu Ala Lys His Gln Gly Ala Arg Tyr Val Trp Asn Arg Thr Glu Leu
    370                 375                 380

Met Gln Ala Ser Leu Asp Pro Ser Val Thr His Leu Met Gly Leu Phe
385                 390                 395                 400

Glu Pro Gly Asp Met Lys Tyr Glu Ile His Arg Asp Ser Thr Leu Asp
                405                 410                 415

Pro Ser Leu Met Glu Met Thr Glu Ala Ala Leu Arg Leu Leu Ser Arg
            420                 425                 430

Asn Pro Arg Gly Phe Phe Leu Phe Val Glu Gly Gly Arg Ile Asp His
        435                 440                 445

Gly His His Glu Ser Arg Ala Tyr Arg Ala Leu Thr Glu Thr Ile Met
    450                 455                 460

Phe Asp Asp Ala Ile Glu Arg Ala Gly Gln Leu Thr Ser Glu Glu Asp
465                 470                 475                 480

Thr Leu Ser Leu Val Thr Ala Asp His Ser His Val Phe Ser Phe Gly
                485                 490                 495

Gly Tyr Pro Leu Arg Gly Ser Ser Ile Phe Gly Leu Ala Pro Gly Lys
            500                 505                 510

Ala Arg Asp Arg Lys Ala Tyr Thr Val Leu Leu Tyr Gly Asn Gly Pro
        515                 520                 525

Gly Tyr Val Leu Lys Asp Gly Ala Arg Pro Asp Val Thr Glu Ser Glu
    530                 535                 540

Ser Gly Ser Pro Glu Tyr Arg Gln Gln Ser Ala Val Pro Leu Asp Gly
545                 550                 555                 560

Glu Thr His Ala Gly Glu Asp Val Ala Val Phe Ala Arg Gly Pro Gln
                565                 570                 575

Ala His Leu Val His Gly Val Gln Glu Gln Thr Phe Ile Ala His Val
            580                 585                 590

Met Ala Phe Ala Ala Cys Leu Glu Pro Tyr Thr Ala Cys Asp Leu Ala
        595                 600                 605

Pro Ser Ala Gly Thr Thr Asp Ala Ala His Pro Gly
    610                 615                 620

<210> SEQ ID NO 14
<211> LENGTH: 683
<212> TYPE: PRT
<213> ORGANISM: Mouse

<400> SEQUENCE: 14

Met Leu Thr Ala Met Leu Leu Ser Cys Val Leu Leu Ala Leu Pro
1               5                   10                  15
```

-continued

```
Pro Thr Leu Gly Val Gln Met Gly Val Ala Pro Leu Lys Gly Ile Arg
             20                  25                  30

Arg Pro Asp Gln Ala Leu Phe Pro Glu Phe Pro Gly Leu Ser Leu Asn
         35                  40                  45

Gly Leu Lys Lys Thr Asn Ala Asp Arg Ala Glu Glu Val Leu Leu Gln
     50                  55                  60

Lys Ala Glu Ala Leu Ala Glu Val Leu Asp Pro Gln Asn Arg Glu Ser
 65                  70                  75                  80

Arg Ser Pro Arg Arg Cys Val Arg Leu His Glu Ser Cys Leu Gly Gln
                 85                  90                  95

Gln Val Pro Cys Cys Asp Pro Cys Ala Thr Cys Tyr Cys Arg Phe Phe
            100                 105                 110

Asn Ala Phe Cys Tyr Cys Arg Lys Leu Gly Thr Ala Met Asn Leu Cys
        115                 120                 125

Ser Arg Thr Met Ser Ile Glu Asn Asn Ile Leu Ile Gly Pro Pro Pro
    130                 135                 140

Tyr Tyr Pro Leu Glu Glu Gly Thr Ala Gly Glu Gln Leu His Arg Ala
145                 150                 155                 160

Ile Ser Arg Tyr Ala Ala Val Pro Gly Thr Leu Ala Tyr Thr Asp Val
                165                 170                 175

His Thr Glu Leu Glu Val Thr Tyr Lys Glu Phe Leu Asp Val Thr Cys
            180                 185                 190

Arg Leu Ala Glu Ala Met Lys Asn Tyr Gly Leu Gly Leu Gln His Thr
        195                 200                 205

Ile Ser Val Cys Ser Glu Asn Cys Val Gln Phe Phe Met Pro Ile Cys
    210                 215                 220

Ala Ala Leu Tyr Val Gly Val Ala Thr Ala Pro Thr Asn Asp Ile Tyr
225                 230                 235                 240

Asn Glu Arg Glu Leu Tyr Asn Ser Leu Ser Ile Ser Gln Pro Thr Val
                245                 250                 255

Val Phe Thr Ser Arg Asn Ser Leu Gln Lys Ile Leu Gly Val Gln Ser
            260                 265                 270

Arg Leu Pro Ile Ile Lys Lys Ile Ile Ile Leu Asp Gly Lys Lys Asp
        275                 280                 285

Tyr Leu Gly Tyr Gln Ser Met Gln Ser Phe Met Lys Glu His Val Pro
    290                 295                 300

Ala Asn Phe Asn Val Ser Ala Phe Lys Pro Leu Ser Phe Asp Leu Asp
305                 310                 315                 320

Arg Val Ala Cys Ile Met Asn Ser Ser Gly Ser Thr Gly Leu Pro Lys
                325                 330                 335

Gly Val Pro Ile Ser His Arg Asn Thr Ile Tyr Arg Phe Ser His Cys
            340                 345                 350

Arg Asp Pro Val Phe Gly Asn Gln Ile Ile Pro Asp Thr Thr Ile Leu
        355                 360                 365

Cys Ala Val Pro Phe His His Ala Phe Gly Thr Phe Thr Asn Leu Gly
    370                 375                 380

Tyr Leu Ile Cys Gly Phe His Val Val Leu Met Tyr Arg Phe Asn Glu
385                 390                 395                 400

His Leu Phe Leu Gln Thr Leu Gln Asp Tyr Lys Cys Gln Ser Ala Leu
                405                 410                 415

Leu Val Pro Thr Val Leu Ala Phe Leu Ala Lys Asn Pro Leu Val Asp
            420                 425                 430
```

```
Lys Tyr Asp Leu Ser Asn Leu His Glu Ile Ala Ser Gly Gly Ala Pro
        435                 440                 445

Leu Ser Lys Glu Ile Ser Glu Ile Ala Ala Lys Arg Phe Lys Leu Pro
    450                 455                 460

Gly Ile Arg Gln Gly Tyr Gly Leu Thr Glu Thr Thr Cys Ala Ile Val
465                 470                 475                 480

Ile Thr Ala Glu Gly Glu Phe Lys Leu Gly Ala Val Gly Lys Val Val
                485                 490                 495

Pro Phe Tyr Ser Leu Lys Val Leu Asp Leu Asn Thr Gly Lys Lys Leu
            500                 505                 510

Gly Pro Asn Glu Arg Gly Glu Ile Cys Phe Lys Gly Pro Met Ile Met
        515                 520                 525

Lys Gly Tyr Ile Asn Asn Pro Glu Ala Thr Arg Glu Leu Ile Asp Glu
    530                 535                 540

Glu Gly Trp Ile His Ser Gly Asp Ile Gly Tyr Phe Asp Glu Asp Gly
545                 550                 555                 560

His Val Tyr Ile Val Asp Arg Leu Lys Ser Leu Ile Lys Tyr Lys Gly
                565                 570                 575

Tyr Gln Val Pro Pro Ala Glu Leu Glu Ala Leu Leu Gln His Pro
            580                 585                 590

Phe Ile Glu Asp Ala Gly Val Ala Gly Val Pro Asp Glu Val Ala Gly
        595                 600                 605

Asp Leu Pro Gly Ala Val Val Leu Lys Glu Gly Lys Ser Ile Thr
610                 615                 620

Glu Lys Glu Ile Gln Asp Tyr Val Ala Gly Gln Val Thr Ser Ser Lys
625                 630                 635                 640

Lys Leu Arg Gly Gly Val Glu Phe Val Lys Glu Val Pro Lys Gly Phe
                645                 650                 655

Thr Gly Lys Ile Asp Thr Arg Lys Ile Lys Glu Ile Leu Ile Lys Ala
            660                 665                 670

Gln Lys Gly Lys Ser Lys Ser Lys Ala Lys Leu
        675                 680

<210> SEQ ID NO 15
<211> LENGTH: 605
<212> TYPE: PRT
<213> ORGANISM: Human

<400> SEQUENCE: 15

Met Leu Thr Ala Ala Leu Leu Ser Cys Ala Leu Leu Ala Leu Pro
 1               5                  10                  15

Ala Thr Arg Gly Ala Gln Met Gly Leu Ala Leu Gln Asp Arg Glu Pro
                20                  25                  30

Arg Ser Ser Arg Arg Cys Val Arg Leu His Glu Ser Cys Leu Gly Gln
            35                  40                  45

Gln Val Pro Cys Cys Asp Pro Cys Ala Thr Cys Tyr Cys Arg Phe Phe
        50                  55                  60

Asn Ala Phe Cys Tyr Cys Arg Lys Leu Gly Thr Ala Met Asn Pro Cys
65                  70                  75                  80

Ser Arg Thr Leu Val Pro Arg Gly Ser Gly Ser Ile Ile Pro Val Glu
                85                  90                  95

Glu Glu Asn Pro Asp Phe Trp Asn Arg Gln Ala Ala Glu Ala Leu Gly
            100                 105                 110

Ala Ala Lys Lys Leu Gln Pro Ala Gln Thr Ala Ala Lys Asn Leu Ile
        115                 120                 125
```

```
Ile Phe Leu Gly Asp Gly Met Gly Val Ser Thr Val Thr Ala Ala Arg
    130                 135                 140

Ile Leu Lys Gly Gln Lys Lys Asp Lys Leu Gly Pro Glu Thr Phe Leu
145                 150                 155                 160

Ala Met Asp Arg Phe Pro Tyr Val Ala Leu Ser Lys Thr Tyr Ser Val
                165                 170                 175

Asp Lys His Val Pro Asp Ser Gly Ala Thr Ala Thr Ala Tyr Leu Cys
            180                 185                 190

Gly Val Lys Gly Asn Phe Gln Thr Ile Gly Leu Ser Ala Ala Ala Arg
        195                 200                 205

Phe Asn Gln Cys Asn Thr Thr Arg Gly Asn Glu Val Ile Ser Val Met
    210                 215                 220

Asn Arg Ala Lys Lys Ala Gly Lys Ser Val Gly Val Thr Thr Thr
225                 230                 235                 240

Arg Val Gln His Ala Ser Pro Ala Gly Ala Tyr Ala His Thr Val Asn
                245                 250                 255

Arg Asn Trp Tyr Ser Asp Ala Asp Val Pro Ala Ser Ala Arg Gln Glu
            260                 265                 270

Gly Cys Gln Asp Ile Ala Thr Gln Leu Ile Ser Asn Met Asp Ile Asp
        275                 280                 285

Val Ile Leu Gly Gly Arg Lys Tyr Met Phe Pro Met Gly Thr Pro
    290                 295                 300

Asp Pro Glu Tyr Pro Asp Asp Tyr Ser Gln Gly Gly Thr Arg Leu Asp
305                 310                 315                 320

Gly Lys Asn Leu Val Gln Glu Trp Leu Ala Lys His Gln Gly Ala Arg
                325                 330                 335

Tyr Val Trp Asn Arg Thr Glu Leu Met Gln Ala Ser Leu Asp Pro Ser
            340                 345                 350

Val Thr His Leu Met Gly Leu Phe Glu Pro Gly Asp Met Lys Tyr Glu
        355                 360                 365

Ile His Arg Asp Ser Thr Leu Asp Pro Ser Leu Met Glu Met Thr Glu
    370                 375                 380

Ala Ala Leu Arg Leu Leu Ser Arg Asn Pro Arg Gly Phe Phe Leu Phe
385                 390                 395                 400

Val Glu Gly Gly Arg Ile Asp His Gly His His Glu Ser Arg Ala Tyr
                405                 410                 415

Arg Ala Leu Thr Glu Thr Ile Met Phe Asp Asp Ala Ile Glu Arg Ala
            420                 425                 430

Gly Gln Leu Thr Ser Glu Glu Asp Thr Leu Ser Leu Val Thr Ala Asp
        435                 440                 445

His Ser His Val Phe Ser Phe Gly Gly Tyr Pro Leu Arg Gly Ser Ser
    450                 455                 460

Ile Phe Gly Leu Ala Pro Gly Lys Ala Arg Asp Arg Lys Ala Tyr Thr
465                 470                 475                 480

Val Leu Leu Tyr Gly Asn Gly Pro Gly Tyr Val Leu Lys Asp Gly Ala
                485                 490                 495

Arg Pro Asp Val Thr Glu Ser Glu Ser Gly Ser Pro Glu Tyr Arg Gln
            500                 505                 510

Gln Ser Ala Val Pro Leu Asp Gly Glu Thr His Ala Gly Glu Asp Val
        515                 520                 525

Ala Val Phe Ala Arg Gly Pro Gln Ala His Leu Val His Gly Val Gln
    530                 535                 540
```

```
Glu Gln Thr Phe Ile Ala His Val Met Ala Phe Ala Ala Cys Leu Glu
545                 550                 555                 560

Pro Tyr Thr Ala Cys Asp Leu Ala Pro Ser Ala Gly Thr Thr Asp Ala
                565                 570                 575

Ala His Pro Gly Lys Leu Gly Pro Glu Gln Lys Leu Ile Ser Glu Glu
            580                 585                 590

Asp Leu Asn Ser Ala Val Asp His His His His His
            595                 600             605

<210> SEQ ID NO 16
<211> LENGTH: 666
<212> TYPE: PRT
<213> ORGANISM: Human

<400> SEQUENCE: 16

Met Leu Thr Ala Ala Leu Leu Ser Cys Ala Leu Leu Ala Leu Pro
1               5                   10                  15

Ala Thr Arg Gly Ala Gln Met Gly Leu Ala Leu Gln Asp Arg Glu Pro
            20                  25                  30

Arg Ser Ser Arg Arg Cys Val Arg Leu His Glu Ser Cys Leu Gly Gln
        35                  40                  45

Gln Val Pro Cys Cys Asp Pro Cys Ala Thr Cys Tyr Cys Arg Phe Phe
    50                  55                  60

Asn Ala Phe Cys Tyr Cys Arg Lys Leu Gly Thr Ala Met Asn Pro Cys
65                  70                  75                  80

Ser Arg Thr Leu Val Pro Arg Gly Ser Gly Ser Met Ser Ile Glu Asn
                85                  90                  95

Asn Ile Leu Ile Gly Pro Pro Tyr Tyr Pro Leu Glu Glu Gly Thr
            100                 105                 110

Ala Gly Glu Gln Leu His Arg Ala Ile Ser Arg Tyr Ala Ala Val Pro
        115                 120                 125

Gly Thr Leu Ala Tyr Thr Asp Val His Thr Glu Leu Glu Val Thr Tyr
    130                 135                 140

Lys Glu Phe Leu Asp Val Thr Cys Arg Leu Ala Glu Ala Met Lys Asn
145                 150                 155                 160

Tyr Gly Leu Gly Leu Gln His Thr Ile Ser Val Cys Ser Glu Asn Cys
                165                 170                 175

Val Gln Phe Phe Met Pro Ile Cys Ala Ala Leu Tyr Val Gly Val Ala
            180                 185                 190

Thr Ala Pro Thr Asn Asp Ile Tyr Asn Glu Arg Glu Leu Tyr Asn Ser
        195                 200                 205

Leu Ser Ile Ser Gln Pro Thr Val Val Phe Thr Ser Arg Asn Ser Leu
    210                 215                 220

Gln Lys Ile Leu Gly Val Gln Ser Arg Leu Pro Ile Ile Lys Lys Ile
225                 230                 235                 240

Ile Ile Leu Asp Gly Lys Lys Asp Tyr Leu Gly Tyr Gln Ser Met Gln
                245                 250                 255

Ser Phe Met Lys Glu His Val Pro Ala Asn Phe Asn Val Ser Ala Phe
            260                 265                 270

Lys Pro Leu Ser Phe Asp Leu Asp Arg Val Ala Cys Ile Met Asn Ser
        275                 280                 285

Ser Gly Ser Thr Gly Leu Pro Lys Gly Val Pro Ile Ser His Arg Asn
    290                 295                 300

Thr Ile Tyr Arg Phe Ser His Cys Arg Asp Pro Val Phe Gly Asn Gln
305                 310                 315                 320
```

```
Ile Ile Pro Asp Thr Thr Ile Leu Cys Ala Val Pro Phe His His Ala
                325                 330                 335
Phe Gly Thr Phe Thr Asn Leu Gly Tyr Leu Ile Cys Gly Phe His Val
            340                 345                 350
Val Leu Met Tyr Arg Phe Asn Glu His Leu Phe Leu Gln Thr Leu Gln
        355                 360                 365
Asp Tyr Lys Cys Gln Ser Ala Leu Leu Val Pro Thr Val Leu Ala Phe
    370                 375                 380
Leu Ala Lys Asn Pro Leu Val Asp Lys Tyr Asp Leu Ser Asn Leu His
385                 390                 395                 400
Glu Ile Ala Ser Gly Gly Ala Pro Leu Ser Lys Glu Ile Ser Glu Ile
                405                 410                 415
Ala Ala Lys Arg Phe Lys Leu Pro Gly Ile Arg Gln Gly Tyr Gly Leu
            420                 425                 430
Thr Glu Thr Thr Cys Ala Ile Val Ile Thr Ala Glu Gly Glu Phe Lys
        435                 440                 445
Leu Gly Ala Val Gly Lys Val Val Pro Phe Tyr Ser Leu Lys Val Leu
    450                 455                 460
Asp Leu Asn Thr Gly Lys Lys Leu Gly Pro Asn Glu Arg Gly Glu Ile
465                 470                 475                 480
Cys Phe Lys Gly Pro Met Ile Met Lys Gly Tyr Ile Asn Asn Pro Glu
                485                 490                 495
Ala Thr Arg Glu Leu Ile Asp Glu Glu Gly Trp Ile His Ser Gly Asp
            500                 505                 510
Ile Gly Tyr Phe Asp Glu Asp Gly His Val Tyr Ile Val Asp Arg Leu
        515                 520                 525
Lys Ser Leu Ile Lys Tyr Lys Gly Tyr Gln Val Pro Pro Ala Glu Leu
    530                 535                 540
Glu Ala Leu Leu Leu Gln His Pro Phe Ile Glu Asp Ala Gly Val Ala
545                 550                 555                 560
Gly Val Pro Asp Glu Val Ala Gly Asp Leu Pro Gly Ala Val Val Val
                565                 570                 575
Leu Lys Glu Gly Lys Ser Ile Thr Glu Lys Glu Ile Gln Asp Tyr Val
            580                 585                 590
Ala Gly Gln Val Thr Ser Lys Lys Leu Arg Gly Gly Val Glu Phe
        595                 600                 605
Val Lys Glu Val Pro Lys Gly Phe Thr Gly Lys Ile Asp Thr Arg Lys
    610                 615                 620
Ile Lys Glu Ile Leu Ile Lys Ala Gln Lys Gly Lys Ser Lys Ser Lys
625                 630                 635                 640
Ala Lys Leu Gly Pro Glu Gln Lys Leu Ile Ser Glu Glu Asp Leu Asn
                645                 650                 655
Ser Ala Val Asp His His His His His
            660                 665

<210> SEQ ID NO 17
<211> LENGTH: 621
<212> TYPE: PRT
<213> ORGANISM: Human

<400> SEQUENCE: 17

Met Leu Thr Ala Ala Leu Leu Ser Cys Ala Leu Leu Leu Ala Leu Pro
 1               5                  10                  15
Ala Thr Arg Gly Ala Gln Met Gly Leu Ala Pro Met Glu Gly Ile Arg
```

-continued

```
                 20                  25                  30
Arg Pro Asp Gln Ala Leu Leu Pro Glu Leu Pro Gly Leu Gly Leu Arg
             35                  40                  45
Ala Pro Leu Lys Lys Thr Asn Ala Glu Gln Ala Glu Glu Asp Leu Leu
         50                  55                  60
Gln Glu Ala Gln Ala Leu Ala Glu Val Leu Asp Leu Gln Asp Arg Glu
 65                  70                  75                  80
Pro Arg Ser Ser Arg Arg Cys Val Arg Leu His Glu Ser Cys Leu Gly
                 85                  90                  95
Gln Gln Val Pro Cys Cys Asp Pro Cys Ala Thr Cys Tyr Cys Arg Phe
                100                 105                 110
Phe Asn Ala Phe Cys Tyr Cys Arg Lys Leu Gly Thr Ala Met Asn Pro
             115                 120                 125
Cys Ser Arg Thr Ile Ile Pro Val Glu Glu Glu Asn Pro Asp Phe Trp
         130                 135                 140
Asn Arg Gln Ala Ala Glu Ala Leu Gly Ala Lys Lys Leu Gln Pro
145                 150                 155                 160
Ala Gln Thr Ala Ala Lys Asn Leu Ile Ile Phe Leu Gly Asp Gly Met
                165                 170                 175
Gly Val Ser Thr Val Thr Ala Ala Arg Ile Leu Lys Gly Gln Lys Lys
             180                 185                 190
Asp Lys Leu Gly Pro Glu Thr Phe Leu Ala Met Asp Arg Phe Pro Tyr
         195                 200                 205
Val Ala Leu Ser Lys Thr Tyr Ser Val Asp Lys His Val Pro Asp Ser
 210                 215                 220
Gly Ala Thr Ala Thr Ala Tyr Leu Cys Gly Val Lys Gly Asn Phe Gln
225                 230                 235                 240
Thr Ile Gly Leu Ser Ala Ala Arg Phe Asn Gln Cys Asn Thr Thr
                245                 250                 255
Arg Gly Asn Glu Val Ile Ser Val Met Asn Arg Ala Lys Lys Ala Gly
             260                 265                 270
Lys Ser Val Gly Val Val Thr Thr Thr Arg Val Gln His Ala Ser Pro
         275                 280                 285
Ala Gly Ala Tyr Ala His Thr Val Asn Arg Asn Trp Tyr Ser Asp Ala
         290                 295                 300
Asp Val Pro Ala Ser Ala Arg Gln Glu Gly Cys Gln Asp Ile Ala Thr
305                 310                 315                 320
Gln Leu Ile Ser Asn Met Asp Ile Asp Val Ile Leu Gly Gly Gly Arg
                325                 330                 335
Lys Tyr Met Phe Pro Met Gly Thr Pro Asp Pro Glu Tyr Pro Asp Asp
             340                 345                 350
Tyr Ser Gln Gly Gly Thr Arg Leu Asp Gly Lys Asn Leu Val Gln Glu
         355                 360                 365
Trp Leu Ala Lys His Gln Gly Ala Arg Tyr Val Trp Asn Arg Thr Glu
         370                 375                 380
Leu Met Gln Ala Ser Leu Asp Pro Ser Val Thr His Leu Met Gly Leu
385                 390                 395                 400
Phe Glu Pro Gly Asp Met Lys Tyr Glu Ile His Arg Asp Ser Thr Leu
                405                 410                 415
Asp Pro Ser Leu Met Glu Met Thr Glu Ala Ala Leu Arg Leu Leu Ser
             420                 425                 430
Arg Asn Pro Arg Gly Phe Phe Leu Phe Val Glu Gly Gly Arg Ile Asp
         435                 440                 445
```

```
His Gly His His Glu Ser Arg Ala Tyr Arg Ala Leu Thr Glu Thr Ile
    450                 455                 460

Met Phe Asp Asp Ala Ile Glu Arg Ala Gly Gln Leu Thr Ser Glu Glu
465                 470                 475                 480

Asp Thr Leu Ser Leu Val Thr Ala Asp His Ser His Val Phe Ser Phe
                485                 490                 495

Gly Gly Tyr Pro Leu Arg Gly Ser Ser Ile Phe Gly Leu Ala Pro Gly
            500                 505                 510

Lys Ala Arg Asp Arg Lys Ala Tyr Thr Val Leu Leu Tyr Gly Asn Gly
        515                 520                 525

Pro Gly Tyr Val Leu Lys Asp Gly Ala Arg Pro Asp Val Thr Glu Ser
    530                 535                 540

Glu Ser Gly Ser Pro Glu Tyr Arg Gln Gln Ser Ala Val Pro Leu Asp
545                 550                 555                 560

Gly Glu Thr His Ala Gly Glu Asp Val Ala Val Phe Ala Arg Gly Pro
                565                 570                 575

Gln Ala His Leu Val His Gly Val Gln Glu Gln Thr Phe Ile Ala His
            580                 585                 590

Val Met Ala Phe Ala Ala Cys Leu Glu Pro Tyr Thr Ala Cys Asp Leu
        595                 600                 605

Ala Pro Ser Ala Gly Thr Thr Asp Ala Ala His Pro Gly
    610                 615                 620

<210> SEQ ID NO 18
<211> LENGTH: 684
<212> TYPE: PRT
<213> ORGANISM: Human

<400> SEQUENCE: 18

Met Leu Thr Ala Ala Leu Leu Ser Cys Ala Leu Leu Ala Leu Pro
1               5                   10                  15

Ala Thr Arg Gly Ala Gln Met Gly Leu Ala Pro Met Glu Gly Ile Arg
            20                  25                  30

Arg Pro Asp Gln Ala Leu Leu Pro Glu Leu Pro Gly Leu Gly Leu Arg
        35                  40                  45

Ala Pro Leu Lys Lys Thr Asn Ala Glu Gln Ala Glu Glu Asp Leu Leu
    50                  55                  60

Gln Glu Ala Gln Ala Leu Ala Glu Val Leu Asp Leu Gln Asp Arg Glu
65                  70                  75                  80

Pro Arg Ser Ser Arg Arg Cys Val Arg Leu His Glu Ser Cys Leu Gly
                85                  90                  95

Gln Gln Val Pro Cys Cys Asp Pro Cys Ala Thr Cys Tyr Cys Arg Phe
            100                 105                 110

Phe Asn Ala Phe Cys Tyr Cys Arg Lys Leu Gly Thr Ala Met Asn Pro
        115                 120                 125

Cys Ser Arg Thr Met Ser Ile Glu Asn Asn Ile Leu Ile Gly Pro Pro
    130                 135                 140

Pro Tyr Tyr Pro Leu Glu Gly Thr Ala Gly Glu Gln Leu His Arg
145                 150                 155                 160

Ala Ile Ser Arg Tyr Ala Ala Val Pro Gly Thr Leu Ala Tyr Thr Asp
                165                 170                 175

Val His Thr Glu Leu Glu Val Thr Tyr Lys Glu Phe Leu Asp Val Thr
            180                 185                 190

Cys Arg Leu Ala Glu Ala Met Lys Asn Tyr Gly Leu Gly Leu Gln His
```

-continued

```
            195                 200                 205
Thr Ile Ser Val Cys Ser Glu Asn Cys Val Gln Phe Met Pro Ile
    210                 215                 220
Cys Ala Ala Leu Tyr Val Gly Val Ala Thr Ala Pro Thr Asn Asp Ile
225                 230                 235                 240
Tyr Asn Glu Arg Glu Leu Tyr Asn Ser Leu Ser Ile Ser Gln Pro Thr
                245                 250                 255
Val Val Phe Thr Ser Arg Asn Ser Leu Gln Lys Ile Leu Gly Val Gln
                260                 265                 270
Ser Arg Leu Pro Ile Ile Lys Lys Ile Ile Ile Leu Asp Gly Lys Lys
    275                 280                 285
Asp Tyr Leu Gly Tyr Gln Ser Met Gln Ser Phe Met Lys Glu His Val
    290                 295                 300
Pro Ala Asn Phe Asn Val Ser Ala Phe Lys Pro Leu Ser Phe Asp Leu
305                 310                 315                 320
Asp Arg Val Ala Cys Ile Met Asn Ser Ser Gly Ser Thr Gly Leu Pro
                325                 330                 335
Lys Gly Val Pro Ile Ser His Arg Asn Thr Ile Tyr Arg Phe Ser His
                340                 345                 350
Cys Arg Asp Pro Val Phe Gly Asn Gln Ile Ile Pro Asp Thr Thr Ile
                355                 360                 365
Leu Cys Ala Val Pro Phe His His Ala Phe Gly Thr Phe Thr Asn Leu
    370                 375                 380
Gly Tyr Leu Ile Cys Gly Phe His Val Val Leu Met Tyr Arg Phe Asn
385                 390                 395                 400
Glu His Leu Phe Leu Gln Thr Leu Gln Asp Tyr Lys Cys Gln Ser Ala
                405                 410                 415
Leu Leu Val Pro Thr Val Leu Ala Phe Leu Ala Lys Asn Pro Leu Val
                420                 425                 430
Asp Lys Tyr Asp Leu Ser Asn Leu His Glu Ile Ala Ser Gly Gly Ala
    435                 440                 445
Pro Leu Ser Lys Glu Ile Ser Glu Ile Ala Ala Lys Arg Phe Lys Leu
    450                 455                 460
Pro Gly Ile Arg Gln Gly Tyr Gly Leu Thr Glu Thr Thr Cys Ala Ile
465                 470                 475                 480
Val Ile Thr Ala Glu Gly Glu Phe Lys Leu Gly Ala Val Gly Lys Val
                485                 490                 495
Val Pro Phe Tyr Ser Leu Lys Val Leu Asp Leu Asn Thr Gly Lys Lys
                500                 505                 510
Leu Gly Pro Asn Glu Arg Gly Glu Ile Cys Phe Lys Gly Pro Met Ile
    515                 520                 525
Met Lys Gly Tyr Ile Asn Asn Pro Glu Ala Thr Arg Glu Leu Ile Asp
    530                 535                 540
Glu Glu Gly Trp Ile His Ser Gly Asp Ile Gly Tyr Phe Asp Glu Asp
545                 550                 555                 560
Gly His Val Tyr Ile Val Asp Arg Leu Lys Ser Leu Ile Lys Tyr Lys
                565                 570                 575
Gly Tyr Gln Val Pro Pro Ala Glu Leu Glu Ala Leu Leu Gln His
                580                 585                 590
Pro Phe Ile Glu Asp Ala Gly Val Ala Gly Val Pro Asp Glu Val Ala
    595                 600                 605
Gly Asp Leu Pro Gly Ala Val Val Val Leu Lys Glu Gly Lys Ser Ile
    610                 615                 620
```

```
Thr Glu Lys Glu Ile Gln Asp Tyr Val Ala Gly Gln Val Thr Ser Ser
625                 630                 635                 640

Lys Lys Leu Arg Gly Gly Val Glu Phe Val Lys Glu Val Pro Lys Gly
            645                 650                 655

Phe Thr Gly Lys Ile Asp Thr Arg Lys Ile Lys Glu Ile Leu Ile Lys
            660                 665                 670

Ala Gln Lys Gly Lys Ser Lys Ser Lys Ala Lys Leu
            675                 680
```

<210> SEQ ID NO 19
<211> LENGTH: 621
<212> TYPE: PRT
<213> ORGANISM: Human

<400> SEQUENCE: 19

```
Met Leu Thr Ala Ala Leu Leu Ser Cys Ala Leu Leu Ala Leu Pro
1               5                   10                  15

Ala Thr Arg Gly Ala Gln Met Gly Leu Ala Ile Ile Pro Val Glu Glu
            20                  25                  30

Glu Asn Pro Asp Phe Trp Asn Arg Gln Ala Ala Glu Ala Leu Gly Ala
            35                  40                  45

Ala Lys Lys Leu Gln Pro Ala Gln Thr Ala Ala Lys Asn Leu Ile Ile
    50                  55                  60

Phe Leu Gly Asp Gly Met Gly Val Ser Thr Val Thr Ala Ala Arg Ile
65              70                  75                  80

Leu Lys Gly Gln Lys Lys Asp Lys Leu Gly Pro Glu Thr Phe Leu Ala
                85                  90                  95

Met Asp Arg Phe Pro Tyr Val Ala Leu Ser Lys Thr Tyr Ser Val Asp
            100                 105                 110

Lys His Val Pro Asp Ser Gly Ala Thr Ala Thr Ala Tyr Leu Cys Gly
            115                 120                 125

Val Lys Gly Asn Phe Gln Thr Ile Gly Leu Ser Ala Ala Ala Arg Phe
130                 135                 140

Asn Gln Cys Asn Thr Thr Arg Gly Asn Glu Val Ile Ser Val Met Asn
145                 150                 155                 160

Arg Ala Lys Lys Ala Gly Lys Ser Val Gly Val Val Thr Thr Thr Arg
                165                 170                 175

Val Gln His Ala Ser Pro Ala Gly Ala Tyr Ala His Thr Val Asn Arg
            180                 185                 190

Asn Trp Tyr Ser Asp Ala Asp Val Pro Ala Ser Ala Arg Gln Glu Gly
            195                 200                 205

Cys Gln Asp Ile Ala Thr Gln Leu Ile Ser Asn Met Asp Ile Asp Val
    210                 215                 220

Ile Leu Gly Gly Gly Arg Lys Tyr Met Phe Pro Met Gly Thr Pro Asp
225                 230                 235                 240

Pro Glu Tyr Pro Asp Asp Tyr Ser Gln Gly Gly Thr Arg Leu Asp Gly
            245                 250                 255

Lys Asn Leu Val Gln Glu Trp Leu Ala Lys His Gln Gly Ala Arg Tyr
            260                 265                 270

Val Trp Asn Arg Thr Glu Leu Met Gln Ala Ser Leu Asp Pro Ser Val
            275                 280                 285

Thr His Leu Met Gly Leu Phe Glu Pro Gly Asp Met Lys Tyr Glu Ile
    290                 295                 300

His Arg Asp Ser Thr Leu Asp Pro Ser Leu Met Glu Met Thr Glu Ala
```

305                 310                 315                 320

Ala Leu Arg Leu Leu Ser Arg Asn Pro Arg Gly Phe Phe Leu Phe Val
                325                 330                 335

Glu Gly Gly Arg Ile Asp His Gly His His Glu Ser Arg Ala Tyr Arg
            340                 345                 350

Ala Leu Thr Glu Thr Ile Met Phe Asp Asp Ala Ile Glu Arg Ala Gly
        355                 360                 365

Gln Leu Thr Ser Glu Glu Asp Thr Leu Ser Leu Val Thr Ala Asp His
    370                 375                 380

Ser His Val Phe Ser Phe Gly Tyr Pro Leu Arg Gly Ser Ser Ile
385                 390                 395                 400

Phe Gly Leu Ala Pro Gly Lys Ala Arg Asp Arg Lys Ala Tyr Thr Val
                405                 410                 415

Leu Leu Tyr Gly Asn Gly Pro Gly Tyr Val Leu Lys Asp Gly Ala Arg
            420                 425                 430

Pro Asp Val Thr Glu Ser Glu Ser Gly Ser Pro Glu Tyr Arg Gln Gln
        435                 440                 445

Ser Ala Val Pro Leu Asp Gly Glu Thr His Ala Gly Glu Asp Val Ala
    450                 455                 460

Val Phe Ala Arg Gly Pro Gln Ala His Leu Val His Gly Val Gln Glu
465                 470                 475                 480

Gln Thr Phe Ile Ala His Val Met Ala Phe Ala Ala Cys Leu Glu Pro
                485                 490                 495

Tyr Thr Ala Cys Asp Leu Ala Pro Ser Ala Gly Thr Thr Asp Ala Ala
            500                 505                 510

His Pro Gly Pro Met Glu Gly Ile Arg Arg Pro Asp Gln Ala Leu Leu
        515                 520                 525

Pro Glu Leu Pro Gly Leu Gly Leu Arg Ala Pro Leu Lys Lys Thr Asn
    530                 535                 540

Ala Glu Gln Ala Glu Glu Asp Leu Leu Gln Glu Ala Gln Ala Leu Ala
545                 550                 555                 560

Glu Val Leu Asp Leu Gln Asp Arg Glu Pro Arg Ser Ser Arg Arg Cys
                565                 570                 575

Val Arg Leu His Glu Ser Cys Leu Gly Gln Gln Val Pro Cys Cys Asp
            580                 585                 590

Pro Cys Ala Thr Cys Tyr Cys Arg Phe Phe Asn Ala Phe Cys Tyr Cys
        595                 600                 605

Arg Lys Leu Gly Thr Ala Met Asn Pro Cys Ser Arg Thr
    610                 615                 620

<210> SEQ ID NO 20
<211> LENGTH: 684
<212> TYPE: PRT
<213> ORGANISM: Human

<400> SEQUENCE: 20

Met Leu Thr Ala Ala Leu Leu Ser Cys Ala Leu Leu Ala Leu Pro
1               5                   10                  15

Ala Thr Arg Gly Ala Gln Met Gly Leu Ala Met Ser Ile Glu Asn Asn
                20                  25                  30

Ile Leu Ile Gly Pro Pro Tyr Tyr Pro Leu Glu Gly Thr Ala
            35                  40                  45

Gly Glu Gln Leu His Arg Ala Ile Ser Arg Tyr Ala Ala Val Pro Gly
        50                  55                  60

-continued

```
Thr Leu Ala Tyr Thr Asp Val His Thr Glu Leu Glu Val Thr Tyr Lys
 65                  70                  75                  80

Glu Phe Leu Asp Val Thr Cys Arg Leu Ala Glu Ala Met Lys Asn Tyr
                 85                  90                  95

Gly Leu Gly Leu Gln His Thr Ile Ser Val Cys Ser Glu Asn Cys Val
            100                 105                 110

Gln Phe Phe Met Pro Ile Cys Ala Ala Leu Tyr Val Gly Val Ala Thr
        115                 120                 125

Ala Pro Thr Asn Asp Ile Tyr Asn Glu Arg Glu Leu Tyr Asn Ser Leu
130                 135                 140

Ser Ile Ser Gln Pro Thr Val Val Phe Thr Ser Arg Asn Ser Leu Gln
145                 150                 155                 160

Lys Ile Leu Gly Val Gln Ser Arg Leu Pro Ile Ile Lys Lys Ile Ile
                165                 170                 175

Ile Leu Asp Gly Lys Lys Asp Tyr Leu Gly Tyr Gln Ser Met Gln Ser
            180                 185                 190

Phe Met Lys Glu His Val Pro Ala Asn Phe Asn Val Ser Ala Phe Lys
        195                 200                 205

Pro Leu Ser Phe Asp Leu Asp Arg Val Ala Cys Ile Met Asn Ser Ser
210                 215                 220

Gly Ser Thr Gly Leu Pro Lys Gly Val Pro Ile Ser His Arg Asn Thr
225                 230                 235                 240

Ile Tyr Arg Phe Ser His Cys Arg Asp Pro Val Phe Gly Asn Gln Ile
                245                 250                 255

Ile Pro Asp Thr Thr Ile Leu Cys Ala Val Pro Phe His His Ala Phe
            260                 265                 270

Gly Thr Phe Thr Asn Leu Gly Tyr Leu Ile Cys Gly Phe His Val Val
        275                 280                 285

Leu Met Tyr Arg Phe Asn Glu His Leu Phe Leu Gln Thr Leu Gln Asp
290                 295                 300

Tyr Lys Cys Gln Ser Ala Leu Leu Val Pro Thr Val Leu Ala Phe Leu
305                 310                 315                 320

Ala Lys Asn Pro Leu Val Asp Lys Tyr Asp Leu Ser Asn Leu His Glu
                325                 330                 335

Ile Ala Ser Gly Gly Ala Pro Leu Ser Lys Glu Ile Ser Glu Ile Ala
            340                 345                 350

Ala Lys Arg Phe Lys Leu Pro Gly Ile Arg Gln Gly Tyr Gly Leu Thr
        355                 360                 365

Glu Thr Thr Cys Ala Ile Val Ile Thr Ala Glu Gly Glu Phe Lys Leu
370                 375                 380

Gly Ala Val Gly Lys Val Val Pro Phe Tyr Ser Leu Lys Val Leu Asp
385                 390                 395                 400

Leu Asn Thr Gly Lys Lys Leu Gly Pro Asn Glu Arg Gly Glu Ile Cys
                405                 410                 415

Phe Lys Gly Pro Met Ile Met Lys Gly Tyr Ile Asn Asn Pro Glu Ala
            420                 425                 430

Thr Arg Glu Leu Ile Asp Glu Glu Gly Trp Ile His Ser Gly Asp Ile
        435                 440                 445

Gly Tyr Phe Asp Glu Asp Gly His Val Tyr Ile Val Asp Arg Leu Lys
450                 455                 460

Ser Leu Ile Lys Tyr Lys Gly Tyr Gln Val Pro Pro Ala Glu Leu Glu
465                 470                 475                 480

Ala Leu Leu Leu Gln His Pro Phe Ile Glu Asp Ala Gly Val Ala Gly
```

```
                    485                 490                 495
Val Pro Asp Glu Val Ala Gly Asp Leu Pro Gly Ala Val Val Leu
                500                 505                 510
Lys Glu Gly Lys Ser Ile Thr Glu Lys Glu Ile Gln Asp Tyr Val Ala
                515                 520                 525
Gly Gln Val Thr Ser Ser Lys Lys Leu Arg Gly Gly Val Glu Phe Val
                530                 535                 540
Lys Glu Val Pro Lys Gly Phe Thr Gly Lys Ile Asp Thr Arg Lys Ile
545                 550                 555                 560
Lys Glu Ile Leu Ile Lys Ala Gln Lys Gly Lys Ser Lys Ser Lys Ala
                565                 570                 575
Lys Leu Pro Met Glu Gly Ile Arg Arg Pro Asp Gln Ala Leu Leu Pro
                580                 585                 590
Glu Leu Pro Gly Leu Gly Leu Arg Ala Pro Leu Lys Lys Thr Asn Ala
                595                 600                 605
Glu Gln Ala Glu Glu Asp Leu Leu Gln Glu Ala Gln Ala Leu Ala Glu
                610                 615                 620
Val Leu Asp Leu Gln Asp Arg Glu Pro Arg Ser Ser Arg Arg Cys Val
625                 630                 635                 640
Arg Leu His Glu Ser Cys Leu Gly Gln Gln Val Pro Cys Cys Asp Pro
                645                 650                 655
Cys Ala Thr Cys Tyr Cys Arg Phe Phe Asn Ala Phe Cys Tyr Cys Arg
                660                 665                 670
Lys Leu Gly Thr Ala Met Asn Pro Cys Ser Arg Thr
                675                 680

<210> SEQ ID NO 21
<211> LENGTH: 37
<212> TYPE: DNA
<213> ORGANISM: Human

<400> SEQUENCE: 21
gggctcggcg gtcctgcagg gccaagccca tctgggc                        38

<210> SEQ ID NO 22
<211> LENGTH: 20
<212> TYPE: DNA
<213> ORGANISM: Human

<400> SEQUENCE: 22
taatacgact cactataggg                                           28

<210> SEQ ID NO 23
<211> LENGTH: 18
<212> TYPE: DNA
<213> ORGANISM: Human

<400> SEQUENCE: 23
ctgcaggacc gcgagccc                                             18

<210> SEQ ID NO 24
<211> LENGTH: 18
<212> TYPE: DNA
<213> ORGANISM: Human

<400> SEQUENCE: 24
gtcgacggcg ctattcag                                             18
```

US 6,878,520 B1

C-TERMINAL REGION OF AGOUTI-RELATED TRANSCRIPT (ART) PROTEIN

CROSS-REFERENCE TO RELATED APPLICATIONS

This application is a § 371 of PCT/US98/26457, filed Dec. 11, 1998, which claims the benefit of U.S. provisional application 60/069,747, filed Dec. 16, 1997.

STATEMENT REGARDING FEDERALLY-SPONSORED R&D

Not applicable

REFERENCE TO MICROFICHE APPENDIX

Not applicable

FIELD OF THE INVENTION

The present invention is directed to polypeptides derived from the C-terminal region of the agouti-related transcript (ART) protein and to uses of such polypeptides, including use as inhibitors of the binding of melanocyte stimulating hormones to melanocortin receptors, and use to identify inhibitors of the binding of ART protein to melanocortin receptors.

BACKGROUND OF THE INVENTION

ART (agouti related transcript) was originally discovered as an mRNA that is upregulated in the hypothalamus of ob/ob and db/db mice. The ART gene has been cloned from both mice and humans and encodes a protein of 131 amino acids in mice and 132 amino acids in humans (Shutter et al., 1997, Genes and Development 11:593–602). Recombinantly produced ART protein has been shown to be a functional antagonist of the melanocortin-3 receptor (MC3R) and the melanocortin-4 receptor (MC4R) (Fong et al., 1997, Biochem. Biophys. Res. Comm. 237:629–631; Ollman et al., 1997, Science 278:135–138).

MC3R and MC4R belong to a class of G-protein coupled receptors known as the melanocortin receptors, since these receptors activate adenylyl cyclase in response to ligands known as melanocortins (e.g., adrenocorticotrophin (ACTH) and the α-, β-, and γ-melanocyte stimulating hormones). MC3R and MC4R are neural melanocortin receptors, with MC3R being expressed in the hypothalamus and limbic system of the brain and MC4R being expressed widely in the brain. In particular, MC4R expression has been found in a number of hypothalamic sites, including the ventromedial, lateral, dorsomedial, and paraventricular nuclei (Mountjoy et al., 1994, Mol. Endocrinol. 8:1298–1308), regions which have been shown to play a role in feeding behavior (Bray, 1987, Nutr. Rev. 45:3343). Gene targeting experiments have shown that MC4R has an important role in the control of feeding behavior and obesity. Knockout mice lacking MC4R develop an obesity syndrome characterized by hyperphagia, hyperinsulinemia, and hyperglycemia (Huszar et al., 1997, Cell 88:131–141).

In view of this, there is great interest in the ART protein, which appears to be a natural regulator of MC3R and MC4R in humans. It is believed that the ART protein is likely to be a natural regulator of human obesity which functions by antagonizing either MC3R or MC4R. Accordingly, the identification of substances that inhibit the binding of ART protein to MC3R or MC4R is desirable, since such inhibitors are likely to be of value in the control of obesity. Substances that potentiate the effect of ART protein on MC3R or MC4R are also likely to be of value in the control of body weight.

SUMMARY OF THE INVENTION

The present invention provides novel polypeptides derived from the C-terminal region of the human and mouse ART proteins. Also provided are DNA sequences encoding the novel C-terminal polypeptides. The novel C-terminal polypeptides can be used to inhibit the binding of melanocyte stimulating hormones to melanocortin receptors. Methods of identifying inhibitors of the effect of ART protein on the binding of melanocyte stimulating hormones to melanocortin receptors are also provided.

DETAILED DESCRIPTION OF THE INVENTION

Figure 1:
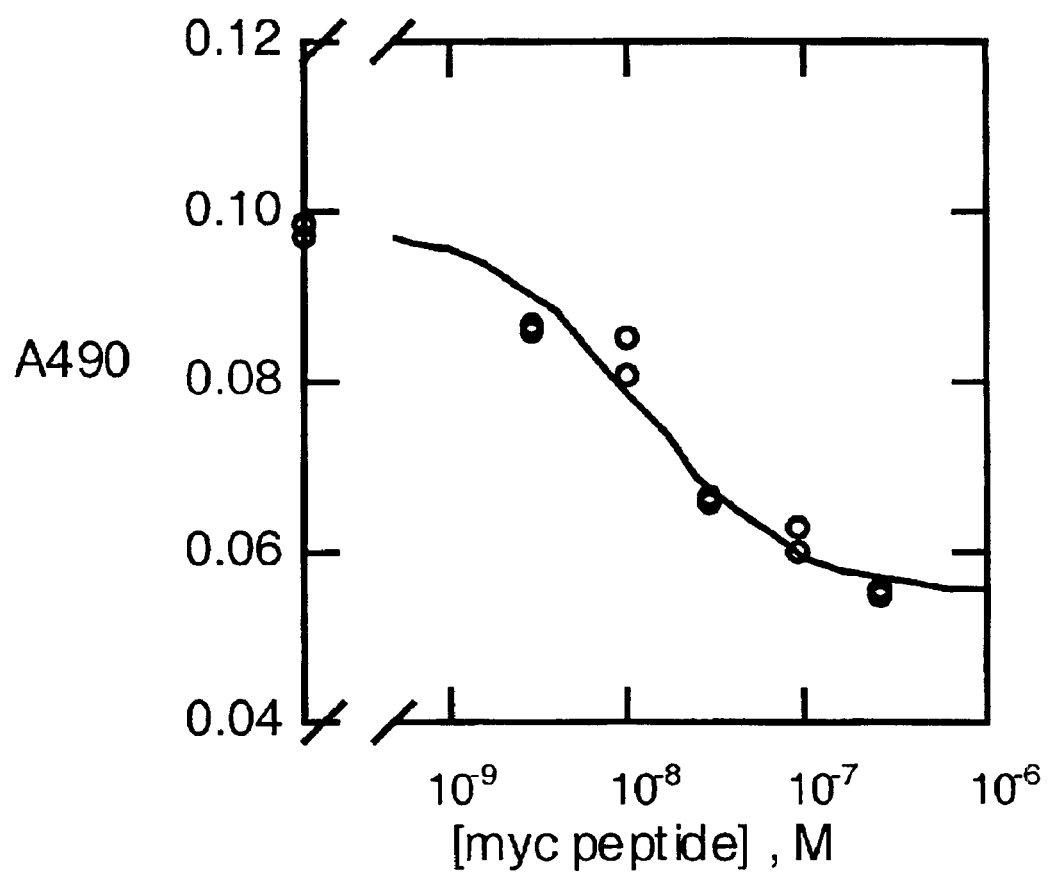
FIG. 1 shows the quantitation of c-ART-b from COS-7 cells through the use of an ELISA using an antibody that recognizes the myc epitope in c-ART-b. Shown is the standard curve generated using known amounts of myc peptide. For the c-ART-b preparation made from COS-7 cells, a 10× dilution of the sample gave an absorbance of 0.079, corresponding to 10 nM in the above standard curve. Therefore, the c-ART-b preparation had a concentration of 100 nM.

The present invention provides C-terminal polypeptides derived from the agouti-related transcript (ART) protein and DNA sequences encoding those polypeptides. The C-terminal polypeptides from the ART protein are referred to herein as "ART polypeptides". In certain embodiments, the ART polypeptides are present in a contiguous polypeptide sequence, i.e., a fusion protein, that incorporates, generally at the C-terminus of the fusion protein, one or more amino acid sequences not derived from the ART protein. Such non-ART protein sequences can be, e.g., "tags", such as a protein kinase A site (for easier radioisotope labeling) or an antigenic sequence (e.g., a myc epitope) for ELISA quantitation. Other tags are known in the art and ART polypeptides incorporating such other tags are included in the present invention. In other embodiments, the ART polypeptides are present in a fusion protein with another protein that gives rise to an easily detectable signal, e.g., alkaline phosphatase (ART-AP) or luciferase (ART-luc). Fusion proteins such as ART-AP or ART-luc are useful in binding assays since their presence and/or concentration can be detected without the use of radioactivity.

In particular, the present invention includes the following ART polypeptides:

c-ART-a: This polypeptide contains, from N to C terminus: (1) a yeast signal sequence peptide; (2) amino acids 76–132 of the human ART protein; (3) a thrombin site; (4) a myc epitope; (5) a protein kinase A (PKA)

site; and (6) a hexahistidine tag. The amino acid sequence of c-ART-a is:

<u>MNIFYIFLFLLSFVQGLEHTHRRGSLVKRSSLQDREPRS</u>
                                    1

SRRCVRLHESCLGQQVPCCDPCATCYCRFFNAFCYCRKLG
                    2

TAMNPCSRT<u>LVPRGS</u>EQKLISEEDLN<u>LRRASLG</u>HHHHHH
         3                4       5    6

(SEQ.ID.NO.:1)

c-ART-b: This polypeptide contains, from N to C terminus: (1) amino acids 1–26 of the human ART protein; (2) amino acids 76–132 of the human ART protein; (3) a thrombin site; (4) a myc epitope; and (5) a hexahistidine tag. The amino acid sequence of c-ART-b is:

<u>MLTAALLSCALLLALPATRGAQMGLAL</u>QDREPRSSRRCVRL
                1

HESCLGQQVPCCDPCATCYCRFFNAFCYCRKLGTAMNPCS
                    2

RT<u>LVPRGS</u>GSELGTKLGPEQKLISEEDLNSAVD<u>HHHHHH</u>
    3           4                       5

(SEQ.ID.NO.:2)

c-ART-c: This polypeptide contains, from N to C terminus: (1) amino acids 1–26 of the human ART protein; (2) amino acids 76–132 of the human ART protein; (3) a thrombin site; (4) a PKA site; (5) a myc epitope; and (6) a hexahistidine tag. The amino acid sequence of c-ART-c is:

<u>MLTAALLSCALLLALPATRGAQMGLAL</u>QDREPRSSRRCVRL
                1

HESCLGQQVPCCDPCATCYCRFFNAFCYCRKLGTAMNPCSRT
                    2

<u>LVPRGS</u>GSL<u>RRASLG</u>K<u>LEQKLISEEDLNSAVD</u>HHHHHH
    3       4       5                   6

(SEQ.ID.NO.:3)

ART-AP: This polypeptide contains, from N to C terminus: (1) amino acids 1–132 of the human ART protein; (2) a thrombin site; (3) the alkaline phosphatase protein; (4) a myc epitope; and (5) a hexahistidine tag. The amino acid sequence of ART-AP is:

<u>MLTAALLSCALLLALPATRGAQMGLAPMEGIRRPDQALLP</u>

<u>ELPGLGLRAPLKKTNAEQAEEDLLQEAQALAEVLDLQDRE</u>
                                1

<u>PRSSRRCVRLHESCLGQQVPCCDPCATCYCRFFNAFCYCR</u>

<u>KLGTAMNPCSRTLVPRGSGS</u>IIPVEEENPDFWNRQAAEAL
                2

GAAKKLQPAQTAAKNLIIFLGDGMGVSTVTAARILKGQKK

DKLGPETFLAMDRFPYVALSKTYSVDKHVPDSGATATAYL

CGVKGNFQTIGLSAAARFNQCNTTRGNEVISVMNRAKKAG

KSVGVVTTTRVQHASPAGAYAHTVNRNWYSDADVPASA

RQEGCQDIATQLISNMDIDVILGGGRKYMFPMGTPDPEY

PDDYSQGGTRLDGKNLVQEWLAKHQGARYVWNRTELM

QASLDPSVTHLMGLFEPGDMKYEIHRDSTLDPSLMEMTE
                    3

AALRLLSRNPRGFFLFVEGGRIDHGHHESRAYRALTETIM

FDDAIERAGQLTSEEDTLSVTADHSHVFSFGGYPLRGSS

IFGLAPGKARDRKAYTVLLYGNGPGYVLKDGARPDVTES

ESGSPEYRQQSAVPLDGETHAGEDVAVFARGPQAHLVHG

VQEQTFIAHVMAFAACLEPYTACDLAPSAGTTDAAHPG

KLGPEQKLISEEDLNSAVD<u>HHHHHH</u>
        4               5

(SEQ.ID.NO.:4)

ART-luc: This polypeptide contains, from N to C terminus: (1) amino acids 1–132 of the human ART protein; (2) a thrombin site; (3) the luciferase protein; (4) a myc epitope; and (5) a hexahistidine tag. The amino acid sequence of ART-luc is:

<u>MLTAALLSCALLLALPATRGAQMGLAPMEGIRRPDQALLP</u>

<u>ELPGLGLRAPLKKTNAEQAEEDLLQEAQALAEVLDLQDRE</u>
                                1

<u>PRSSRRCVRLHESCLGQQVPCCDPCATCYCRFFNAFCYCR</u>

<u>KLGTAMNPCSRTLVPRGSGS</u><u>MSIENNILIGPPPYYPLEEG</u>
                2

TAGEQLHRAISRYAAVPGTLAYTDVHTELEVTYKEFLDVT

CRLAEAMKNYGLGLQHTISVCSENCVQFFMPICAALYVG

VATAPTNDIYNERELYNSLSISQPTVVFTSRNSLQKILGVQ

SRLPIIKKIIILDGKKDYLGYQSMQSFMKEHVPANFNVSA

FKPLSFDLDRVACIMNSSGSTGLPKGVPISHRNTIYRFSH

CRDPVFGNQIIPDTTILCAVPFHHAFGTFTNLGYLICGFH

VVLMYRFNEHLFLQTLQDYKCQSALLVPTVLAFLAKNPL
                        3

VDKYDLSNLHEIASGGAPLSKEISEIAAKRFKLPGIRQGYG

LTETTCAIVITAEGEFKLGAVGKVVPFYSLKVLDLNTGKK

LGPNERGEICFKGPMIMKGYINNPEATRELIDEEGWIHSG

DIGYFDEDGHVYIVDRLKSLIKYKGYQVPPAELEALLLQH

PFIEDAGVAGVPDEVAGDLPGAVVVLKEGKSITEKEIQDY

VAGQVTSSKKLRGGVEFVKEVPKGFTGKIDTRKIKEILIK

AQKGKSKSKAKLGPEQKLISEEDLNSAVD<u>HHHHHH</u>
                    4               5

(SEQ.ID.NO.:5)

The present invention also includes an ART polypeptide containing amino acids 1–26 and 76–132 of the human ART protein, having the following polypeptide sequence:

MLTAALLSCALLLALPATRGAQMGLALQDREPRSSRRCVRL

HESCLGQQVPCCDPCATCYCRFFNAFCYCRKLGTAMNPCSRT (SEQ.ID.NO.:6)

The present invention also includes an ART polypeptide containing amino acids 76–132 of the human ART protein, having the following polypeptide sequence:

LQDREPRSSRRCVRLHESCLGQQVPCCDPCATCYCRFFNAFCYCRKLGTA

MNPCSRT (SEQ.ID.NO.:7)

The present invention also includes an ART polypeptide containing amino acids 1–26 and 75–131 of the mouse ART protein, having the following polypeptide sequence:

MLTAMLLSCVLLLALPPTLGVQMGVAPQNRESRSPRRCVRL

HESCLGQQVPCCDPCATCYCRFFNAFCYCRKLGTAMNLCSRT (SEQ.ID.NO.:8)

The present invention also includes an ART polypeptide containing amino acids 75–131 of the mouse ART protein, having the following polypeptide sequence:

PQNRESRSPRRCVRLHESCLGQQVPCCDPCATCYCRFFNAFCYCRKLGTA

MNLCSRT (SEQ.ID.NO.:9)

The present invention also includes an ART polypeptide having the following sequence, from N to C terminus: (1) a yeast signal sequence peptide; (2) amino acids 75–131 of the mouse ART protein; (3) a thrombin site; (4) a myc epitope; (5) a PKA site; and (6) a hexahistidine tag. The amino acid sequence of this ART polypeptide is:

MNIFYIFLFLLSFVQGLEHTHRRGSLVKRSSPQNRESRSPRRCVRL
                    1

HESCLGQQVPCCDPCATCYCRFFNAFCYCRKLGTAMNLCSRT
                    2
LVPRGSEQKLISEEDLNLRRASLGHHHHHH
  3      4         5      6

(SEQ.ID.NO.:10)

The present invention also includes an ART polypeptide having the following sequence, from N to C terminus: (1) amino acids 1–26 of the mouse ART protein; (2) amino acids 75–131 of the mouse ART protein; (3) a thrombin site; (4) a myc epitope; and (5) a hexahistidine tag. The amino acid sequence of this ART polypeptide is:

MLTAMLLSCVLLLALPPTLGVQMGVAPQNRESRSPRRCVRL
                    1

HESCLGQQVPCCDPCATCYCRFFNAFCYCRKLGTAMNLCSRT
                    2

LVPRGSEQKLISEEDLNLRRASLSHHHHHH
  3      4         5      6

(SEQ.ID.NO.:11)

The present invention also includes an ART polypeptide having the following sequence, from N to C terminus: (1) amino acids 1–26 of the mouse ART protein; (2) amino acids 75–131 of the mouse ART protein; (3) a thrombin site; (4) a PKA site; (5) a myc epitope; and (6) a hexahistidine tag. The amino acid sequence of this ART polypeptide is:

MLTAMLLSCVLLLALPPTLGVQMGVAPQNRESRSPRRCVRL
                    1

HESCLGQQVPCCDPCATCYCRFFNAFCYCRKLGTAMNLCSRT
                    2

LVPRGSGSLRRASLGKLEQKLISEEDLNHHHHHH
  3    4            5          6

(SEQ.ID.NO.:12)

The present invention also includes an ART polypeptide, having the following sequence, from N to C terminus: (1) amino acids 1–131 of the mouse ART protein; and (2) the alkaline phosphatase protein. The amino acid sequence of this polypeptide is:

MLTAMLLSCVLLLALPPTLGVQMGVAPLKGIRRPDQAL

FPEFPGLSLNGLKKTNADRAEEVLLQKAEALAEVLDP
                    1

QNRESRSPRRCVRLHESCLGQQVPCCDPCATCYCRFFN

AFCYCRKLGTAMNLCSRTIIPVEEENPDFWNRQAAEAL

GAAKKLQPAQTAAKNLIIFLGDGMGVSTVTAARILKGQKK

DKLGPETFLAMDRFPYVALSKTYSVDKHVPDSGATATAYL

CGVKGNFQTIGLSAAARFNQCNTTRGNEVISVMNRAKKAG

KSVGVVTTTRVQHASPAGAYAHTVNRNWYSDADVPASA

RQEGCQDIATQLISNMDIDVILGGGRKYMFPMGTPDPEY

PDDYSQGGTRLDGKNLVQEWLAKHQGARYVWNRTELM

QASLDPSVTHLMGLFEPGDMKYEIHRDSTLDPSLMEMTE
                    2

ALLRLLSRNPRGFFLFVEGGRIDHGHHESRAYRALTETIM

FDDAIERAGQLTSEEDTLSLVTADHSHVFSFGGYPLRGSS

IFGLAPGKARDRKAYTVLLYGNGPGYVLKDGARPDVTES

ESGSPEYRQQSAVPLDGETHAGEDVAVFARGPQAHLVHG

VQEQTFIAHVMAFAACLEPYTACDLAPSAGTTDAAHPG (SEQ.ID.NO.:13)

The present invention also includes an ART polypeptide, having the following sequence, from N to C terminus: (1) amino acids 1–131 of the mouse ART protein; and (2) the luciferase protein. The amino acid sequence of this polypeptide is:

MLTAMLLSCVLLLALPPTLGVQMGVAPLKGIRRPDQALFP

EFPGLSLNGLKKTNADRAEEVLLQKAEALAEVLDPQNRES
                    1

RSPRRCVRLHESCLGQQVPCCDPCATCYCRFFNAFCYCRK

LGTAMNLCSRTMSIENNILIGPPPYYPLEEGTAGEQLHR

AISRYAAVPGTLAYTDVHTELEVTYKEFLDVTCRLAEA

MKNYGLGLQHTISVCSENCVQFFMPICAALYVGVATAP

-continued
TNDIYNERELYNSLSISQPTVVFTSRNSLQKILGVQSR

LPIIKKIIILDGKKDYLGYQSMQSFMKEHVPANFNVSA

FKPLSFDLDRVACIMNSSGSTGLPKGVPISHRNTIYRFSH

CRDPVFGNQIIPDTTILCAVPFHHAFGTFTNLGYLICGFH

VVLMYRFNEHLFLQTLQDYKCQSALLVPTVLAFLAKNPL
2

VDKYDLSNLHEIASGGAPLSKEISEIAAKRFKLPGIRQGYG

LTETTCAIVITAEGEFKLGAVGKVVPFYSLKVLDLNTGKK

LGPNERGEICFKGPMIMKGYINNPEATRELIDEEGWIHSG

DIGYFDEDGHVYIVDRLKSLIKYKGYQVPPAELEALLLQH

PFIEDAGVAGVPDEVAGDLPGAVVVLKEGKSITEKEIQDY

VAGQVTSSKKLRGGVEFVKEVPKGFTGKIDTRKIKEILIK

AQKGKSKSKAKL (SEQ.ID.NO.:14)

The present invention also includes an ART polypeptide, having the following sequence, from N to C terminus: (1) amino acids 1–26 of the human ART protein; (2) amino acids 76–132 of the human ART protein; (3) a thrombin site; (4) the alkaline phosphatase protein; (5) a myc epitope; and (6) a hexahistidine tag. The amino acid sequence of this polypeptide is:

<u>MLTAALLSCALLLALPATRGAQMGLAL</u>QDREPRSSRRCV
1

RLHESCLGQQVPCCDPCATCYCRFFNAFCYCRKLGTA
2

MNPCSRT<u>LVPRGSGS</u>IIPVEEENPDFWNRQAAEAL
3

GAAKKLQPAQTAAKNLIIFLGDGMGVSTVTAARILKGQKK

DKLGPETFLAMDRFPYVALSKTYSVDKHVPDSGATATAYL

CGVKGNFQTIGLSAAARFNQCNTTRGNEVISVMNRAKKAG

KSVGVVTTTRVQHASPAGAYAHTVNRNWYSDADVPASA

RQEGCQDIATQLISNMDIDVILGGGRKYMFPMGTPDPEY

PDDYSQGGTRLDGKNLVQEWLAKHQGARYVWNRTELM

QASLDPSVTHLMGLFEPGDMKYEIHRDSTLDPSLMEMTE
4

AALRLLSRNPRGFFLFVEGGRIDHGHHESRAYRALTETIM

FDDAIERAGQLTSEEDTLSLVTADHSHVFSFGGYPLRGSS

IFGLAPGKARDRKAYTVLLYGNGPGYVLKDGARPDVTES

ESGSPEYRQQSAVPLDGETHAGEDVAVFARGPQAHLVHG

VQEQTFIAHVMAFAACLEPYTACDLAPSAGTTDAAHPG

<u>KLGPEQKLISEEDLN</u>SAVDHHHHHH
5      6

(SEQ.ID.NO.:15)

The present invention also includes an ART polypeptide, having the following sequence, (1) amino acids 1–26 of the human ART protein; (2) amino acids 76–132 of the human ART protein; (3) a thrombin site; (4) the luciferase protein; (5) a myc epitope; and (6) a hexahistidine tag. The amino acid sequence of this polypeptide is:

<u>MLTAALLSCALLLALPATRGAQMGLAL</u>QDREPRSSRRC
1

VRLHESCLGQQVPCCDPCATCYCRFFNAFCYCRKLGTA
2

MNPCSRT<u>LVPRGSGS</u>MSIENNILIGPPPYYPLEEGTAGEQLHR
3

AISRYAAVPGTLAYTDVHTELEVTYKEFLDVTCRLAEA

MKNYGLGLQHTISVCSENCVQFFMPICAALYVGVATAP

TNDIYNERELYNSLSISQPTVVFTSRNSLQKILGVQSR

LPIIKKIIILDGKKDYLGYQSMQSFMKEHVPANFNVSA

FKPLSFDLDRVACIMNSSGSTGLPKGVPISHRNTIYRFSH

CRDPVFGNQIIPDTTILCAVPFHHAFGTFTNLGYLICGFH

VVLMYRFNEHLFLQTLQDYKCQSALLVPTVLAFLAKNPL
4

VDKYDLSNLHEIASGGAPLSKEISEIAAKRFKLPGIRQGYG

LTETTCAIVITAEGEFKLGAVGKVVPFYSLKVLDLNTGKK

LGPNERGEICFKGPMIMKGYINNPEATRELIDEEGWIHSG

DIGYFDEDGHVYIVDRLKSLIKYKGYQVPPAELEALLLQH

PFIEDAGVAGVPDEVAGDLPGAVVVLKEGKSITEKEIQDY

VAGQVTSSKKLRGGVEFVKEVPKGFTGKIDTRKIKEILIK

AQKGKSKSKAKL<u>GPEQKLISEEDLN</u>SAVDHHHHHH
5      6

(SEQ.ID.NO.:16)

The present invention also includes an ART polypeptide having the following sequence, from N to C terminus: (1) amino acids 1–132 of the human ART protein; and (2) the alkaline phosphatase protein. The amino acid sequence of this polypeptide is:

<u>MLTAALLSCALLLALPATRGAQMGLAPMEGIRRPDQALLP</u>

<u>ELPGLGLRAPLKKTNAEQAEEDLLQEAQALAEVLDLQDRE</u>
1

<u>PRSSRRCVRLHESCLGQQVPCCDPCATCYCRFFNAFCYCR</u>

<u>KLGTA</u>MNPCSRTIIPVEEENPDFWNRQAAEALGAAKKLQPA

QTAAKNLIIFLGDGMGVSTVTAARILKGQKKDKLGPETF

LAMDRFPYVALSKTYSVDKHVPDSGATATAYLCGVKGN

FQTIGLSAAARFNQCNTTRGNEVISVMNRAKKAGKSVG

VVTTTRVQHASPAGAYAHTVNRNWYSDADVPASARQ

EGCQDIATQLISNMDIDVILGGGRKYMFPMGTPDPEY

PDDYSQGGTRLDGKNLVQEWLAKHQGARYVWNRTELM

QASLDPSVTHLMGLFEPGDMKYEIHRDSTLDPSLMEMTE
2

AALRLLSRNPRGFFLFVEGGRIDHGHHESRAYRALTETIM

-continued

FDDAIERAGQLTSEEDTLSLVTADHSHVFSFGGYPLRGSS

IFGLAPGKARDRKAYTVLLYGNGPGYVLKDGARPDVTES

ESGSPEYRQQSAVPLDGETHAGEDVAVFARGPQAHLVHG

VQEQTFIAHVMAFAACLEPYTACDLAPSAGTTDAAHPG (SEQ.ID.NO.:17)

The present invention also includes an ART polypeptide having the following sequence, from N to C terminus: (1) amino acids 1–132 of the human ART protein; and (2) the luciferase protein. The amino acid sequence of this polypeptide is:

MLTAALLSCALLLALPATRGAQMGLAPMEGIRRPDQALLP

ELPGLGLRAPLKKTNAEQAEEDLLQEAQALAEVLDLQDRE
1

PRSSRRCVRLHESCLGQQVPCCDPCATCYCRFFNAFCYCR

KLGTAMNPCSRTMSIENNILIGPPPYYPLEEGTAGEQLH

RAISRYAAVPGTLAYTDVHTELEVTYKEFLDVTCRLAE

AMKNYGLGLQHTISVCSENCVQFFMPICAALYVGVAT

APTNDIYNERELYNSLSISQPTVVFTSRNSLQKILGVQ

SRLPIIKKIIILDGKKDYLGYQSMQSFMKEHVPANFNVSA

FKPLSFDLDRVACIMNSSGSTGLPKGVPISHRNTIYRFSH

CRDPVFGNQIIPDTTILCAVPFHHAFGTFTNLGYLICGFH

VVLMYRFNEHLFLQTLQDYKCQSALLVPTVLAFLAKNPL
2
VDKYDLSNLHEIASGGAPLSKEISEIAAKRFKLPGIRQGYG

LTETTCAIVITAEGEFKLGAVGKVVPFYSLKVLDLNTGKK

LGPNERGEICFKGPMIMKGYINNPEATRELIDEEGWIHSG

DIGYFDEDGHVYIVDRLKSLIKYKGYQVPPAELEALLLQH

PFIEDAGVAGVPDEVAGDLPGAVVVLKEGKSITEKEIQDY

VAGQVTSSKKLRGGVEFVKEVPKGFTGKIDTRKIKEILIK

AQKGKSKSKAKL (SEQ.ID.NO.:18)

The present invention also includes an ART polypeptide having the following sequence, from N to C terminus: (1) amino acids 1–26 of the human ART protein; (2) the alkaline phosphatase protein; (3) amino acids 27–132 of the human ART protein. The amino acid sequence is:

MLTAALLSCALLLALPATRGAQMGLAIIPVEEENPDFWNRQAAEAL
1

GAAKKLQPAQTAAKNLIIFLGDGMGVSTVTAARILKGQKK

DKLGPETFLAMDRFPYVALSKTYSVDKHVPDSGATATAYL

CGVKGNFQTIGLSAAARFNQCNTTRGNEVISVMNRAKKAG

KSVGVVTTTRVQHASPAGAYAHTVNRNWYSDADVPASA

RQEGCQDIATQLISNMDIDVILGGGRKYMFPMGTPDPEY

PDDYSQGGTRLDGKNLVQEWLAKHQGARYVWNRTELM

-continued

QASLDPSVTHLMGLFEPGDMKYEIHRDSTLDPSLMEMTE
2

AALRLLSRNPRGFFLFVEGGRIDHGHHESRAYRALTETIM

FDDAIERAGQLTSEEDTLSLVTADHSHVFSFGGYPLRGSS

IFGLAPGKARDRKAYTVLLYGNGPGYVLKDGARPDVTES

ESGSPEYRQQSAVPLDGETHAGEDVAVFARGPQAHLVHG

VQEQTFIAHVMAFAACLEPYTACDLAPSAGTTDAAHPG

PMEGIRRPDQALLPELPGLGLRAPLKKTNAEQAEEDLLQE
3

AQALAEVLDLQDREPRSSRRCVRLHESCLGQQVPCCDPC

ATCYCRFFNAFCYCRKLGTAMNPCSRT (SEQ.ID.NO.:19)

The present invention also includes an ART polypeptide having the following sequence, from N to C terminus: (1) amino acids 1–26 of the human ART protein; (2) the luciferase protein; (3) amino acids 27–132 of the human ART protein. The amino acid sequence is:

MLTAALLSCALLLALPATRGAQMGLAMSIENNILIGPPPYYPLEEG
1

TAGEQLHRAISRYAAVPGTLAYTDVHTELEVTYKEFLDVT

CRLAEAMKNYGLGLQHTISVCSENCVQFFMPICAALYVG

VATAPTNDIYNERELYNSLSISQPTVVFTSRNSLQKILGVQ

SRLPIIKKIIILDGKKDYLGYQSMQSFMKEHVPANFNVSA

FKPLSFDLDRVACIMNSSGSTGLPKGVPISHRNTIYRFSH

CRDPVFGNQIIPDTTILCAVPFHHAFGTFTNLGYLICGFH

VVLMYRFNEHLFLQTLQDYKCQSALLVPTVLAFLAKNPL
2

VDKYDLSNLHEIASGGAPLSKEISEIAAKRFKLPGIRQGYG

LTETTCAIVITAEGEFKLGAVGKVVPFYSLKVLDLNTGKK

LGPNERGEICFKGPMIMKGYINNPEATRELIDEEGWIHSG

DIGYFDEDGHVYIVDRLKSLIKYKGYQVPPAELEALLLQH

PFIEDAGVAGVPDEVAGDLPGAVVVLKEGKSITEKEIQDY

VAGQVTSSKKLRGGVEFVKEVPKGFTGKIDTRKIKEILIK

AQKGKSKSKAKLPMEGIRRPDQALLPELPGLGLRAPLKK

TNAEQAEEDLLQEAQALAEVLDLQDREPRSSRRCVRLHE
3

SCLGQQVPCCDPCATCYCRFFNAFCYCRKLGTAMNPCSRT (SEQ.ID.NO.:20)

The ART polypeptides of the present invention can be in a form that is substantially free from other polypeptides. "Substantially free from other polypeptides" means at least 90%, preferably 95%, more preferably 99%, and even more preferably 99.9%, free of other proteins. Thus, an ART polypeptide preparation that is substantially free from other polypeptides will contain, as a percent of its total polypeptides, no more than 10%, preferably no more than 5%, more preferably no more than 1%, and even more preferably no more than 0.1%, of non-ART polypeptides. Whether a given ART polypeptide preparation is substantially free from other polypeptides can be determined by such conventional techniques as, e.g., sodium dodecyl sulfate polyacrylamide gel electrophoresis (SDS-PAGE) combined with appropriate staining methods, e.g., silver staining.

It is possible to modify many of the amino acids of the ART polypeptides of the present invention and still retain substantially the same biological activity as possessed by the unmodified ART polypeptide. A modified ART polypeptide has "substantially the same biological activity" as an unmodified ART polypeptide if the modified polypeptide has an $IC_{50}$ value for the inhibition of $^{125}I$-labeled NDP-α-MSH binding to MC3R or MC4R that is no more than 5-fold greater than the $IC_{50}$ value of the unmodified ART polypeptide for the inhibition of $^{125}I$-labeled NDP-α-MSH binding to MC3R or MC4R.

Thus the present invention includes modified ART polypeptides which have amino acid deletions, additions, or substitutions but that still retain substantially the same biological activity as the unmodified ART polypeptide from which they are derived. It is generally accepted that single amino acid substitutions at non-critical positions do not usually alter the biological activity of a protein or polypeptide (see, e.g., *Molecular Biology of the Gene*, Watson et al., 1987, Fourth Ed., The Benjamin/Cummings Publishing Co., Inc., page 226; and Cunningham & Wells, 1989, Science 244:1081–1085). Accordingly, the present invention includes modified polypeptides where one amino acid substitution has been made in SEQ.ID.NOs.:1–20 wherein the modified polypeptides still retain substantially the same biological activity as the unmodified ART polypeptides. The present invention also includes modified polypeptides where two amino acid substitutions have been made in SEQ.ID.NOs.:1–20 wherein the polypeptides still retain substantially the same biological activity as the unmodified ART polypeptides. More generally, the present invention includes modified polypeptides where amino acid substitutions have been made in regions of the polypeptides that are not critical, i.e., in regions where modifications result in a polypeptide with substantially the same biological activity as the unmodified polypeptide.

In particular, the present invention includes embodiments where the above-described substitutions are conservative substitutions. A "conservative amino acid substitution" refers to the replacement of one amino acid residue by another, chemically similar, amino acid residue. Examples of such conservative substitutions are: substitution of one hydrophobic residue (isoleucine, leucine, valine, or methionine) for another; substitution of one polar residue for another polar residue of the same charge (e.g., arginine for lysine; glutamic acid for aspartic acid).

The present invention also includes DNA sequences encoding polypeptides having the amino acid sequences of SEQ.ID.NOs.:1–20, with the proviso that, In the case of the DNA sequences encoding SEQ.ID.NOs.:6–9, the DNA sequences do not encode any contiguous stretch of amino acids from the ART protein other than SEQ.ID.NOs.:6–9.

The DNA sequences of the present invention can be in a form that is substantially free from other nucleic acids. "Substantially free from other nucleic acids" means at least 90%, preferably 95%, more preferably 99%, and even more preferably 99.9%, free of other nucleic acids. Thus, a preparation of DNA sequences encoding an ART polypeptide that is substantially free from other nucleic acids will contain, as a percent of its total nucleic acids, no more than 10%, preferably no more than 5%, more preferably no more than 1%, and even more preferably no more than 0.1%, of nucleic acids other than the DNA sequences encoding ART polypeptides. Whether a given preparation of DNA sequences encoding an ART polypeptide is substantially free from other nucleic acids can be determined by such conventional techniques as, e.g., agarose gel electrophoresis combined with appropriate staining methods, e.g., ethidium bromide staining.

The DNA sequences of the present invention encoding ART polypeptides can be linked with other DNA sequences, e.g., DNA sequences to which DNA sequences encoding the ART protein are not naturally linked, to form "recombinant DNA molecules" encoding ART polypeptides. Such other sequences can include DNA sequences that control transcription or translation such as, e.g., translation initiation sequences, promoters for RNA polymerase II, transcription or translation termination sequences, enhancer sequences, sequences that control replication in microorganisms, or that confer antibiotic resistance. The DNA sequences of the present invention can be inserted into vectors such as plasmids, cosmids, viral vectors, or yeast artificial chromosomes.

Included in the present invention are DNA sequences that hybridize to the DNA sequences encoding ART polypeptides under stringent conditions. By way of example and not limitation, a procedure using conditions of high stringency is as follows: Prehybridization of filters containing DNA is carried out for 2 hr. to overnight at 65° C. in buffer composed of 6×SSC, 5× Denhardt's solution, and 100 µg/ml denatured salmon sperm DNA. Filters are hybridized for 12 to 48 hrs at 65° C. in prehybridization mixture containing 100 µg/ml denatured salmon sperm DNA and 5–20×10$^6$ cpm of $^{32}$P-labeled probe. Washing of filters is done at 37° C. for 1 hr in a solution containing 2×SSC, 0.1% SDS. This is followed by a wash in 0.1×SSC, 0.1% SDS at 50° C. for 45 min. before autoradiography.

Other procedures using conditions of high stringency would include either a hybridization carried out in 5×SSC, 5× Denhardt's solution, 50% formamide at 42° C. for 12 to 48 hours or a washing step carried out in 0.2×SSPE, 0.2% SDS at 65° C. for 30 to 60 minutes.

Reagents mentioned in the foregoing procedures for carrying out high stringency hybridization are well known in the art. Details of the composition of these reagents can be found in, e.g., Sambrook, Fritsch, and Maniatis, 1989, *Molecular Cloning: A Laboratory Manual*, second edition, Cold Spring Harbor Laboratory Press. In addition to the foregoing, other conditions of high stringency which may be used are well known in the art.

Another aspect of the present invention includes host cells that have been engineered to contain and/or express DNA sequences encoding ART polypeptides. Such recombinant host cells can be cultured under suitable conditions to produce ART polypeptides. An expression vector containing DNA encoding ART polypeptides can be used for expression of ART polypeptides in a recombinant host cell. Recombinant host cells may be prokaryotic or eukaryotic, including but not limited to, bacteria such as *E. coli*, fungal cells such as yeast, mammalian cells including, but not limited to, cell lines of human, bovine, porcine, monkey and rodent origin, and insect cells including but not limited to *Drosophila* and silkworm derived cell lines. Cell lines derived from mammalian species which are suitable for recombinant expression of ART polypeptides and which are commercially available, include but are not limited to, L cells L-M(TK-) (ATCC CCL 1.3), L cells L-M (ATCC CCL 1.2), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C1271 (ATCC CRL 1616), BS-C-1 (ATCC CCL 26) and MRC-5 (ATCC CCL 171).

A variety of mammalian expression vectors can be used to express ART polypeptides in mammalian cells. Commercially available mammalian expression vectors which are suitable include, but are not limited to, pMC1neo (Stratagene), pSG5 (Stratagene), pcDNAI and pcDNAIamp, pcDNA3, pcDNA3.1, pCR3.1 (Invitrogen), EBO-pSV2-neo (ATCC 37593), pBPV-1(8-2) (ATCC 37110), pdBPV-MMTneo(342-12) (ATCC 37224), pRSVgpt (ATCC 37199), pRSVneo (ATCC 37198), and pSV2-dhfr (ATCC 37146). Following expression in recombinant cells, ART polypeptides can be purified by conventional techniques to a level that is substantially free from other proteins.

The present invention includes a method of determining whether a substance is an inhibitor of the binding of an ART polypeptide to a melanocortin receptor. Such substances are likely to be useful in the control of body weight. The method takes advantage of the fact that ART polypeptides inhibit the binding of melanocyte stimulating hormones to melanocortin receptors by themselves binding to the receptor. Thus, a substance that antagonizes the inhibitory effect of ART polypeptides on the binding of melanocyte stimulating hormones to melanocortin receptors is likely to act by inhibiting the binding of the ART polypeptide itself to the melanoncortin receptor. The method comprises:

(a) providing cells expressing the melanocortin receptor;

(b) exposing the cells to a chosen concentration of the melanocyte stimulating hormone in the absence of the ART polypeptide and in the absence of the substance and measuring the amount of melanocyte stimulating hormone binding to the cells to obtain a first value for melanocyte stimulating hormone binding;

(c) exposing the cells to the chosen concentration of melanocyte stimulating hormone in the presence of a chosen concentration of the ART polypeptide and in the absence of the substance and measuring the amount of melanocyte stimulating hormone binding to obtain a second value for melanocyte stimulating hormone binding where the second value for melanocyte stimulating hormone binding indicates that less melanocyte stimulating hormone binding has occurred as compared to the first value for melanocyte stimulating hormone binding;

(d) exposing the cells to the chosen concentration of melanocyte stimulating hormone in the presence of the chosen concentration of ART polypeptide and in the presence of the substance and measuring the amount of melanocyte stimulating hormone binding to obtain a third value for melanocyte stimulating hormone binding;

where, if the third value for melanocyte stimulating hormone binding is greater than the second value, then the substance is an inhibitor of the binding of the ART polypeptide to the melanocortin receptor.

In a particular embodiment, the cells expressing the melanocortin receptor are cells that naturally express the melanocortin receptor. In another embodiment, the cells expressing the melanocortin receptor do not naturally express the melanocortin receptor but have been transfected with an expression vector that directs the expression of the melanocortin receptor. Transfection is meant to include any method known in the art for the introduction of the expression vector directing the expression of the melanocortin receptor into the cells. For example, transfection includes calcium phosphate or calcium chloride mediated transfection, lipofection, infection with a retroviral construct containing the melanocortin receptor, and electroporation.

In a particular embodiment, the melanocortin receptor is selected from the group consisting of: the melanocortin-3 receptor (MC3R) and the melanocortin-4 receptor (MC4R). In a particular embodiment of the above-described method, the melanocortin receptor is not a Xenopus melanocortin receptor.

The cells that have been transfected with an expression vector that directs the expression of the melanocortin receptor can be prokaryotic cells or eukaryotic cells. In a particular embodiment, the cells that have been transfected with an expression vector that directs the expression of the melanocortin receptor are selected from the group consisting of: yeast cells, mammalian cells, bacterial cells, and insect cells. In a particular embodiment, the cells that have been transfected with an expression vector that directs the expression of the melanocortin receptor are selected from the group consisting of: human cells, mouse cells, rat cells, bovine cells, porcine cells, hamster cells, and monkey cells. In a particular embodiment, the cells that have been transfected with an expression vector that directs the expression of the melanocortin receptor are selected from the group consisting of: L cells L M(TK-) (ATCC CCL 1.3), L cells L-M (ATCC CCL 1.2), 293 cells (ATCC CRL 1573), Raji cells (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C1271 (ATCC CRL 1616), BS-C-1 (ATCC CCL 26) and MRC-5 (ATCC CCL 171). In a particular embodiment, the cells are not Xenopus melanophore cells.

In a particular embodiment, the melanocyte stimulating hormone is selected from the group consisting of: α-melanocyte stimulating hormone, β-melanocyte stimulating hormone, and γ-melanocyte stimulating hormone.

In a particular embodiment, the ART polypeptide has an amino acid sequence selected from the group consisting of: SEQ.ID.NOs. 1–19 and 20.

In particular embodiments of the above-described method, the method is practiced in vitro and the conditions under which the method is practiced are conditions that are typically used in the art for the study of protein-protein interactions: e.g., physiological pH; salt conditions such as those represented by such commonly used buffers as PBS or in tissue culture media; a temperature of about 4° C. to about 55° C.

In particular embodiments of the above-described method, the chosen concentration of the melanocyte stimulating hormone is from 0.05 nM to 2.0 nM, preferably from 0.1 nM to 1.0 nM, and more preferably from 0.2 nM to 0.5 nM.

In particular embodiments of the above-described method, the chosen concentration of the ART polypeptide is from $10^{-12}$ M to $10^{-7}$M.

In particular embodiments of the above-described method, the method is practiced in vitro and the melanocyte stimulating hormone is labeled, e.g., enzymatically, radioactively, or the like, and the amount of binding of the melanocyte stimulating hormone to the melanocortin receptor is measured by determining the amount of label bound to the cells containing the melanocortin receptor.

Steps (b), (c), and (d) of the above-described method can be modified in that, rather than exposing intact cells to the melanocyte stimulating hormone, the ART polypeptide, or the substance, membranes can be prepared from the cells and the membranes can be exposed to the melanocyte stimulating hormone, the ART polypeptide, or the substance. Such a modification utilizing membranes rather than intact cells in methods similar to that described above, although directed to the binding interactions of other ligands and receptors, is well known in the art and is described in, e.g., Hess et al, 1992, Biochem. Biophys. Res. Comm. 184:260–268.

As a further modification of the above-described method, RNA encoding the melanocortin receptor can be prepared as, e.g., by in vitro transcription using a plasmid containing nucleotide sequences encoding the melanocortin receptor under the control of a bacteriophage T7 promoter, and the RNA can be microinjected into *Xenopus* oocytes in order to cause the expression of the melanocortin receptor in the oocytes. These oocytes then take the place of the cells in the above described method.

Once a substance has been identified as an inhibitor of the binding of the ART polypeptide to the melanocortin receptor, that substance can be tested to determine whether it is also an agonist of the melanocortin receptor. Such testing would involve exposing cells that express the melanocortin receptor to the substance, in the absence of the melanocyte stimulating hormone and the ART protein or ART polypeptides, and determining whether the melanocortin receptor is thereby activated by the substance. In this way, an inhibitor of the effect of ART protein on MC3R or MC4R can be identified that has no, or little, MC3R or MC4R agonist activity, but that relieves the inhibition of MC3R or MC4R receptor activity produced by ART protein. In a similar manner, it can be determined whether the substance is an antagonist of the melanocortin receptor.

The present invention also includes a method for determining whether a substance is an inhibitor of the binding of an ART polypeptide to a melanocortin receptor where the method comprises:

(a) providing cells expressing a melanocortin receptor;
(b) exposing the cells to an ART polypeptide in the presence and in the absence of the substance under conditions such that if the substance were not present, the ART polypeptide would bind to the melanocortin receptor;
(c) measuring the amount of binding of the ART polypeptide to the melanocortin receptor in the presence and in the absence of the substance;
where a decrease in the amount of binding of the ART polypeptide to the melanocortin receptor in the presence as compared to the absence of the substance indicates that the substance is an inhibitor of the binding of the ART polypeptide to the melanocortin receptor.

In a particular embodiment, the cells expressing the melanocortin receptor are cells that naturally express the melanocortin receptor. In another embodiment, the cells expressing the melanocortin receptor do not naturally express the melanocortin receptor but have been transfected with an expression vector that directs the expression of the melanocortin receptor. Transfection is meant to include any method known in the art for the introduction of the expression vector directing the expression of the melanocortin receptor into the cells. For example, transfection includes calcium phosphate or calcium chloride mediated transfection, lipofection, infection with a retroviral construct containing the melanocortin receptor, and electroporation.

In a particular embodiment, the melanocortin receptor is selected from the group consisting of: the melanocortin-3 receptor (MC3R) and the melanocortin-4 receptor (MC4R). In a particular embodiment of the above-described method, the melanocortin receptor is not a *Xenopus* melanocortin receptor.

The cells that have been transfected with an expression vector that directs the expression of the melanocortin receptor can be prokaryotic cells or eukaryotic cells. In a particular embodiment, the cells that have been transfected with an expression vector that directs the expression of the melanocortin receptor are selected from the group consisting of: yeast cells, mammalian cells, bacterial cells, and insect cells. In a particular embodiment, the cells that have been transfected with an expression vector that directs the expression of the melanocortin receptor are selected from the group consisting of: human cells, mouse cells, rat cells, bovine cells, porcine cells, hamster cells, and monkey cells. In a particular embodiment, the cells that have been transfected with an expression vector that directs the expression of the melanocortin receptor are selected from the group consisting of: L cells L-M(TK-) (ATCC CCL 1.3), L cells L-M (ATCC CCL 1.2), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26) and MRC-5 (ATCC CCL 171). In a particular embodiment, the cells are not *Xenopus* melanophore cells.

In a particular embodiment, the ART polypeptide has an amino acid sequence selected from the group consisting of: SEQ.ID.NOs.1–19 and 20. In particular embodiments of the above-described method, the ART polypeptide is used in a concentration of from 10–12 M to 10–7 M.

In particular embodiments of the above-described method, the method is practiced in vitro and the conditions are conditions that are typically used in the art for the study of protein-protein interactions: e.g., physiological pH; salt conditions such as those represented by such commonly used buffers as PBS or in tissue culture media; a temperature of about 4° C. to about 55° C.

In particular embodiments of the above-described method, the method is practiced in vitro and the ART polypeptide is labeled, e.g., enzymatically, radioactively, or the like, and the amount of binding of the ART polypeptide to the melanocortin receptor is measured by determining the amount of label bound to the melanocortin receptor. The ART polypeptide will either be radioactively labeled by $^{32}P$, $^{33}P$, or $^{125}I$ (e.g., for c-ART-a or c-ART-c), or non-radioactively labeled (e.g., ART-AP, ART-luc, c-ART-AP or c-ART-luc). In the case of these latter ART polypeptides, the ART polypeptides can be detected by detecting the enzymatic activity of the alkaline phosphatase or luciferase moieties of the polypeptides.

Step (b) of the above-described method can be modified in that, rather than exposing the cells to an ART polypeptide in the presence and in the absence of the substance, membranes can be prepared from the cells and the membranes can be exposed to an ART polypeptide in the presence and in the absence of the substance. Such a modification utilizing membranes rather than cells in methods similar to that described above, although directed to the binding interactions of other ligands and receptors, is well known in the art and is described in, e.g., Hess et al, 1992, Biochem. Biophys. Res. Comm. 184:260–268.

As a further modification of the above-described method, RNA encoding a melanocortin receptor can be prepared as, e.g., by in vitro transcription using a plasmid containing nucleotide sequences encoding a melanocortin receptor under the control of a bacteriophage T7 promoter, and the RNA can be microinjected into *Xenopus* oocytes in order to cause the expression of the melanocortin receptor in the oocytes. These oocytes then take the place of the cells in the above described method.

Once a substance has been identified as an inhibitor of ART binding to a melanocortin receptor, that substance can be tested to determine whether it is also an agonist of the melanocortin receptor. Such testing would involve exposing cells that express the melanocortin receptor to the substance, in the absence of ART protein or ART polypeptides, and determining whether the melanocortin receptor is thereby activated by the substance. In this way, an inhibitor of ART protein binding to MC3R or MC4R may be identified that has no, or little, MC3R or MC4R agonist activity, but that relieves the inhibition of MC3R or MC4R receptor activity produced by ART protein.

The present invention also includes a method for determining whether a substance is an allosteric enhancer of the binding of an ART polypeptide to a melanocortin receptor where the method comprises:

(a) providing cells expressing a melanocortin receptor, (b) exposing the cells to an ART polypeptide in the presence and in the absence of the substance under conditions such that if the substance were not present, the ART polypeptide would bind to the melanocortin receptor;

(c) measuring the amount of binding of the ART polypeptide to the melanocortin receptor in the presence and in the absence of the substance;

where an increase in the amount of binding of the ART polypeptide to the melanocortin receptor in the presence as compared to the absence of the substance indicates that the substance is an allosteric enhancer of the binding of the ART polypeptide to the melanocortin receptor.

In a particular embodiment, the cells expressing the melanocortin receptor are cells that naturally express the melanocortin receptor. In another embodiment, the cells expressing the melanocortin receptor do not naturally express the melanocortin receptor but have been transfected with an expression vector that directs the expression of the melanocortin receptor. Transfection is meant to include any method known in the art for the introduction of the expression vector directing the expression of the melanocortin receptor into the cells. For example, transfection includes calcium phosphate or calcium chloride mediated transfection, lipofection, infection with a retroviral, construct containing the melanocortin receptor, and electroporation.

In a particular embodiment, the melanocortin receptor is selected from the group consisting of: the melanocortin-3 receptor (MC3R) and the melanocortin-4 receptor (MC4R). In a particular embodiment of the above-described method, the melanocortin receptor is not a *Xenopus* melanocortin receptor.

The cells that have been transfected with an expression vector that directs the expression of the melanocortin receptor can be prokaryotic cells or eukaryotic cells. In a particular embodiment, the cells that have been transfected with an expression vector that directs the expression of the melanocortin receptor are selected from the group consisting of: yeast cells, mammalian cells, bacterial cells, and insect cells. In a particular embodiment, the cells that have been transfected with an expression vector that directs the expression of the melanocortin receptor are selected from the group consisting of: human cells, mouse cells, rat cells, bovine cells, porcine cells, hamster cells, and monkey cells. In a particular embodiment, the cells that have been transfected with an expression vector that directs the expression of the melanocortin receptor are selected from the group consisting of: L cells L-M(TK-) (ATCC CCL 1.3), L cells L-M (ATCC CCL 1.2), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C1271 (ATCC CRL 1616), BS-C-1 (ATCC CCL 26) and MRC-5 (ATCC CCL 171). In a particular embodiment, the cells are not *Xenopus* melanophore cells.

In a particular embodiment, the ART polypeptide has an amino acid sequence selected from the group consisting of: SEQ.ID.NOs.1–19 and 20. In particular embodiments of the above-described method, the ART polypeptide is used in a concentration of from $10^{-12}$ M to $10^{-7}$ M.

In particular embodiments of the above-described method, the method is practiced in vitro and the conditions are conditions that are typically used in the art for the study of protein-protein interactions: e.g., physiological pH; salt conditions such as those represented by such commonly used buffers as PBS or in tissue culture media; a temperature of about 4° C. to about 55° C.

In particular embodiments of the above-described method, the method is practiced in vitro and the ART polypeptide is labeled, e.g., enzymatically, radioactively, or the like, and the amount of binding of the ART polypeptide to the melanocortin receptor is measured by determining the amount of label bound to the melanocortin receptor.

Step (b) of the above-described method can be modified in that, rather than exposing the cells to an ART polypeptide in the presence and in the absence of the substance, membranes can be prepared from the cells and the membranes can be exposed to an ART polypeptide in the presence and in the absence of the substance. Such a modification utilizing membranes rather than cells in methods similar to that described above, although directed to the binding interactions of other ligands and receptors, is well known in the art and is described in, e.g., Hess et al, 1992, Biochem. Biophys. Res. Comm. 184:260–268.

As a further modification of the above-described method, RNA encoding a melanocortin receptor can be prepared as, e.g., by in vitro transcription using a plasmid containing nucleotide sequences encoding a melanocortin receptor under the control of a bacteriophage T7 promoter, and the RNA can be microinjected into *Xenopus* oocytes in order to cause the expression of the melanocortin receptor in the oocytes. These oocytes then take the place of the cells in the above described method.

Melanocortin receptors are G-protein coupled receptors that stimulate $G_s$, leading to the production of cAMP (Cone et al., 1996, Recent Prog. Hormone Res. 51:287–318). Thus, the ART polypeptides of the present invention can be used in a method for determining whether a substance is a functional inhibitor of the antagonistic effect of an ART polypeptide on a melanocortin receptor where the method comprises:

(a) providing cells expressing a melanocortin receptor;

(b) exposing the cells to a melanocyte stimulating hormone, thereby activating the melanocortin receptor and leading to the production of cAMP mediated by the melanocortin receptor;

(c) exposing the cells to an ART polypeptide in the presence and in the absence of the substance under conditions such that if the substance were not present, the ART polypeptide would inhibit the production of cAMP mediated by the melanocortin receptor, (d) measuring the amount of cAMP produced the presence and in the absence of the substance;

where an increase in the amount of cAMP produced in the presence as compared to the absence of the substance indicates that the substance is a functional inhibitor of the antagonistic effect of the ART polypeptide on the melanocortin receptor.

In a particular embodiment, the cells expressing the melanocortin receptor are cells that naturally express the melanocortin receptor. In another embodiment, the cells expressing the melanocortin receptor do not naturally express the melanocortin receptor but have been transfected with an expression vector that directs the expression of the melanocortin receptor. Transfection is meant to include any method known in the art for the introduction of the expression vector directing the expression of the melanocortin receptor into the cells. For example, transfection includes calcium phosphate or calcium chloride mediated transfection, lipofection, infection with a retroviral construct containing the melanocortin receptor, and electroporation.

In a particular embodiment, the melanocortin receptor is selected from the group consisting of: the melanocortin-3 receptor (MC3R) and the melanocortin-4 receptor (MC4R). In a particular embodiment of the above-described method, the melanocortin receptor is not a Xenopus melanocortin receptor.

The cells that have been transfected with an expression vector that directs the expression of the melanocortin receptor can be prokaryotic cells or eukaryotic cells. In a particular embodiment, the cells that have been transfected with an expression vector that directs the expression of the melanocortin receptor are selected from the group consisting of: yeast cells, mammalian cells, bacterial cells, and insect cells. In a particular embodiment, the cells that have been transfected with an expression vector that directs the expression of the melanocortin receptor are selected from the group consisting of: human cells, mouse cells, rat cells, bovine cells, porcine cells, hamster cells, and monkey cells. In a particular embodiment, the cells that have been transfected with an expression vector that directs the expression of the melanocortin receptor are selected from the group consisting of: L cells L-M(TK-) (ATCC CCL 1.3), L cells L-M (ATCC CCL 1.2), 293 (ATCC CRL 1573), Raji (ATCC CCL 86), CV-1 (ATCC CCL 70), COS-1 (ATCC CCL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C1271 (ATCC CRL 1616), BS-C-1 (ATCC CCL 26) and MRC-5 (ATCC CCL 171). In a particular embodiment, the cells are not Xenopus melanophore cells.

In a particular embodiment, the melanocyte stimulating hormone is selected from the group consisting of: α-melanocyte stimulating hormone, β-melanocyte stimulating hormone, and γ-melanocyte stimulating hormone.

In a particular embodiment, the ART polypeptide has an amino acid sequence selected from the group consisting of: SEQ.ID.NOs.1–19 and 20.

In particular embodiments of the above-described method, the method is practiced in vitro and the conditions are conditions that are typically used in the art for the study of protein-protein interactions: e.g., physiological pH; salt conditions such as those represented by such commonly used buffers as PBS or in tissue culture media; a temperature of about 4° C. to about 55° C.

Once a substance has been identified as a functional inhibitor of the antagonistic effect of an ART polypeptide on a melanocortin receptor, that substance can be tested to determine whether it is also an agonist of the melanocortin receptor. Such testing would involve exposing cells that express the melanocortin receptor to the substance, in the absence of ART protein or ART polypeptides, and determining whether the melanocortin receptor is thereby activated by the substance. In this way, an inhibitor of ART protein binding to MC3R or MC4R may be developed that has no, or little, MC3R or MC4R agonist activity, but that relieves the inhibition of MC3R or MC4R receptor activity produced by ART protein. In a similar manner, it can be determined whether the substance is an antagonist of the melanocortin receptor.

The ART polypeptides of the present invention can also be used in a method of determining whether a substance is an inhibitor of the effect of an ART polypeptide that makes use of an assay utilizing a Xenopus melanophore cell line (see, e.g., Quillan et al., 1995, Proc. Natl. Acad. Sci. USA 92:2894; Potenza & Lerner, 1992, Pigment Cell Res. 5:372; Ollman et al., 1997, Science 278:135–138). Such a method comprises:

(a) providing a Xenopus melanophore cell line;

(b) exposing the Xenopus melanophore cell line to a chosen concentration of a melanocyte stimulating hormone in the absence of the ART polypeptide and in the absence of the substance and measuring the amount of pigment dispersion to obtain a first value for pigment dispersion;

(c) exposing the Xenopus melanophore cell line to the chosen concentration of α-melanocyte stimulating hormone in the presence of the ART polypeptide and in the absence of the substance and measuring the amount of pigment dispersion to obtain a second value for pigment dispersion where the second value for pigment dispersion indicates that less pigment has been dispersed as compared to the first value for pigment dispersion;

(d) exposing the Xenopus melanophore cell line to the chosen concentration of α-melanocyte stimulating hormone in the presence of the ART polypeptide and in the presence of the substance and measuring the amount of pigment dispersion to obtain a third value for pigment dispersion;

where if the third value for pigment dispersion indicates that more pigment has been dispersed as compared with the second value, then the substance is an inhibitor of the effect of the ART polypeptide.

In a particular embodiment, the melanocyte stimulating hormone is selected from the group consisting of: α-melanocyte stimulating hormone, β-melanocyte stimulating hormone, and γ-melanocyte stimulating hormone.

In a particular embodiment, the ART polypeptide has an amino acid sequence selected from the group consisting of: SEQ.ID.NOs.1–19 and 20.

In particular embodiments of the above-described method, the conditions are conditions that are typically used in the art for the study of protein-protein interactions: e.g., physiological pH; salt conditions such as those represented by such commonly used buffers as PBS or in tissue culture media; a temperature of about 4° C. to about 55° C.

Once a substance has been identified as an inhibitor of the effect of an ART polypeptide, that substance can be tested to determine whether it is also an agonist of the Xenopus melanocortin receptor. Such testing would involve exposing melanophore cells that express the Xenopus melanocortin receptor to the substance, in the absence of ART protein or ART polypeptides, and determining whether the melanocortin receptor is thereby activated by the substance. In this way, an inhibitor of ART protein binding to the *Xenopus* melanocortin receptor can be identified that may be used as a lead to develop ART binding inhibitors for human MC3R or MC4R that have no, or little, MC3R or MC4R agonist activity, but that relieve the inhibition of MC3R or MC4R receptor activity produced by ART protein. In a similar manner, it can be determined whether the substance is an antagonist of the melanocortin receptor.

The present invention includes a method of determining whether a substance is an inhibitor of the binding of an ART polypeptide to a melanocortin receptor comprising:

(a) providing cells expressing the melanocortin receptor;

(b) exposing the cells to a chosen concentration of the melanocyte stimulating hormone and a chosen concentration of the ART polypeptide in the presence and in the absence of the substance and measuring the amount of melanocyte stimulating hormone binding to the cells in the presence and in the absence of the substance;

where an increase in the amount of melanocyte stimulating hormone binding in the presence of the substance indicates that the substance is an inhibitor of the binding of an ART polypeptide to a melanocortin receptor.

In a particular embodiment, the cells expressing the melanocortin receptor are cells that naturally express the melanocortin receptor. In another embodiment, the cells expressing the melanocortin receptor do not naturally express the melanocortin receptor but have been transfected with an expression vector that directs the expression of the melanocortin receptor. Transfection is meant to include any method known in the art for the introduction of the expression vector directing the expression of the melanocortin receptor into the cells. For example, transfection includes calcium phosphate or calcium chloride mediated transfection, lipofection, infection with a retroviral construct containing the melanocortin receptor, and electroporation.

In a particular embodiment, the melanocortin receptor is selected from the group consisting of: the melanocortin-3 receptor (MC3R) and the melanocortin-4 receptor (MC4R). In a particular embodiment of the above-described method, the melanocortin receptor is not a *Xenopus* melanocortin receptor.

The cells that have been transfected with an expression vector that directs the expression of the melanocortin receptor can be prokaryotic cells or eukaryotic cells. In a particular embodiment, the cells that have been transfected with an expression vector that directs the expression of the melanocortin receptor are selected from the group consisting of: yeast cells, mammalian cells, bacterial cells, and insect cells. In a particular embodiment, the cells that have been transfected with an expression vector that directs the expression of the melanocortin receptor are selected firm the group consisting of: human cells, mouse cells, rat cells, bovine cells, porcine cells, hamster cells, and monkey cells. In a particular embodiment, the cells that have been transfected with an expression vector that directs the expression of the melanocortin receptor are selected from the group consisting of: L cells L-M(TK-) (ATCC CCL 1.3), L cells L-M (ATCC CCL 1.2), 293 cells (ATCC CRL 1573), Raji cells (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C1271 (ATCC CRL 1616), BS-C-1 (ATCC CCL 26) and MRC-5 (ATCC CCL 171). In a particular embodiment, the cells are not *Xenopus* melanophore cells.

In a particular embodiment, the melanocyte stimulating hormone is selected from the group consisting of: α-melanocyte stimulating hormone, β-melanocyte stimulating hormone, and γ-melanocyte stimulating hormone.

In a particular embodiment, the ART polypeptide has an amino acid sequence selected from the group consisting of: SEQ.ID.NOs.1–19 and 20.

In particular embodiments of the above-described method, the method is practiced in vitro and the conditions under which the method is practiced are conditions that are typically used in the art for the study of protein-protein interactions: e.g., physiological pH; salt conditions such as those represented by such commonly used buffers as PBS or in tissue culture media; a temperature of about 4° C. to about 55° C.

In particular embodiments of the above-described method, the chosen concentration of the melanocyte stimulating hormone is from 0.05 nM to 2.0 nM, preferably from 0.1 nM to 1.0 nM, and more preferably from 0.2 nM to 0.5 nM.

In particular embodiments of the above-described method, the chosen concentration of the ART polypeptide is from $10^{-12}$ M to $10^{-7}$ M.

In particular embodiments of the above-described method, the method is practiced in vitro and the melanocyte stimulating hormone is labeled, e.g., enzymatically, radioactively, or the like, and the amount of binding of the melanocyte stimulating hormone to the melanocortin receptor is measured by determining the amount of label bound to the cells containing the melanocortin receptor.

Step (b) of the above-described method can be modified in that, rather than exposing intact cells to the melanocyte stimulating hormone, the ART polypeptide, or the substance, membranes can be prepared from the cells and the membranes can be exposed to the melanocyte stimulating hormone, the ART polypeptide, or the substance. Such a modification utilizing membranes rather than intact cells in methods similar to that described above, although directed to the binding interactions of other ligands and receptors, is well known in the art and is described in, e.g., Hess et al, 1992, Biochem. Biophys. Res. Comm. 184:260–268.

As a further modification of the above-described method, RNA encoding the melanocortin receptor can be prepared as, e.g., by in vitro transcription using a plasmid containing nucleotide sequences encoding the melanocortin receptor under the control of a bacteriophage T7 promoter, and the RNA can be microinjected into *Xenopus* oocytes in order to cause the expression of the melanocortin receptor in the oocytes. These oocytes then take the place of the cells in the above described method.

Once a substance has been identified as an inhibitor of the binding of the ART polypeptide to the melanocortin receptor, that substance can be tested to determine whether it is also an agonist of the melanocortin receptor. Such testing would involve exposing cells that express the melanocortin receptor to the substance, in the absence of the melanocyte stimulating hormone and the ART protein or ART polypeptides, and determining whether the melanocortin receptor is thereby activated by the substance. In this way, an inhibitor of the effect of ART protein on MC3R or MC4R can be identified that has no, or little, MC3R or MC4R agonist activity, but that relieves the inhibition of MC3R or MC4R receptor activity produced by ART protein. In a similar manner, it can be determined whether the substance is an antagonist of the melanocortin receptor.

Compared to full-length ART protein, the ART polypeptides of the present invention are smaller, and therefore easier to produce and less likely to be degraded. With respect to such embodiments of the invention as, e.g., c-ART-b, the non-ART protein amino acid sequences added to the C-terminus of the ART sequences do not impair binding or functional activity, and allow $^{32}$P or $^{33}$P labeling without the need to label the ART sequence. Fusion polypeptides such as, e.g., ART-AP or ART-luc, allow the use of non-radioactive methods to detect ART polypeptides in binding assays.

That the ART polypeptides of the present invention having amino acid sequences from non-ART proteins at their C-terminus are functional is surprising. The C-terminus of ART protein is homologous to the C-terminus of the agouti protein, both the ART protein and the agouti protein having a characteristic pattern of cysteine residues in this region. A similar pattern of cysteine residues has been found in certain ion channel blockers from spider and snail toxins. This pattern of cysteines has been proposed to result in the formation of specific disulfide bridges that constrain the toxins into a characteristic three-dimensional structure that is responsible for the toxins' biological activity (Kim et al., 1995, J. Mol. Biol. 250:659–671; hereinafter "Kim"). While the extreme C-terminal amino acids of the toxin studied by Kim were not part of this three-dimensional structure, these extreme C-terminal amino acids were nevertheless "crucially important," since altering them resulted in a loss of activity. See page 665, right column of Kim: "These results suggest that the C-terminal segment of ω-AGA-IVA is crucially important for its blocking action on the P-type calcium channel expressed in rat cerebellar Purkinje cells." Thus, one would have expected that altering the C-terminus of the ART protein, e.g., by linking it to sequences from a non-ART protein, would have resulted in an ART fusion polypeptide which would lack the activity of the full-length ART protein, or at least show substantially less activity. The present invention demonstrates that this is not so.

The following non-limiting examples are presented to better illustrate the invention.

EXAMPLE 1

Production of a Construct Expressing c-ART-b

The expression plasmid for c-ART-b was constructed by modifying the ART expression plasmid which was generated by inserting the ART cDNA into the EcoRI and BamHI sites of pcDNA3.1-Myc-His-A (Fong et al., 1997, Biochem. Biophys. Res. Comm. 237:629–631; hereinafter "Fong"). The c-ART-b sequence differs from that of the recombinant ART as described by Fong in that residues 27–75 were deleted from ART. To accomplish that, a first PCR was carried out using the ART expression plasmid as template and two oligos (GGGCTCGGCGGTCCTGCAGGG CCAAGCCCATCTGGGC (SEQ.ID.NO.:21); and the T7 primer TAATACGACTCACTATAGGG (SEQ.ID.NO.:22)) to amplify the DNA fragment encoding ART residues 1–26 followed immediately by residues 76–81. A second PCR was carried out using the ART expression plasmid as template and two other oligos (CTGCAGGACCGCGAGCCC (SEQ.ID.NO.:23); and the pcDNA3.1A primer GTCGACG- GCGCTATTCAG (SEQ.ID.NO.:24)) to amplify the DNA fragment encoding ART residues 76–132. A third PCR was then carried out using the first and the second PCR products as template and two oligos (the T7 primer and the pcDNA3.1A primer) to amplify the c-ART-b cDNA. The final PCR product was cleaved by the restriction enzymes EcoRI and BamHI, and ligated to the pcDNA3.1-Myc-His-A vector similarly cleaved by EcoRI and BamHI. The thrombin site sequence was based on the thrombin site in pET-34b (Novagen, Milwaukee, Wis.). The Myc epitope sequence and hexahistine sequence were contained within the pcDNA3.1-Myc-His-A vector (Invitrogen, Carlsbad, Calif.).

EXAMPLE 2

Expression of c-ART-b

COS-7 cells in T-175 flasks were transiently transfected with the c-ART-b expression plasmid (24 μg) by lipofectamine (Gibco), and grown in Opti-mem media (Gibco) supplemented with 1% fetal bovine serum. Two days after transfection, culture media were collected, centrifuged to remove residual cells, concentrated about 100-fold in Centriprep-3 (Amicon) and stored at 4° C. in the presence of 2.5 mM EGTA, 4 mg/ml leupeptin, and 0.01 mM phosphoramidon. After determination of the concentration of c-ART-b, NaN$_3$ was added to 0.02%. Determination of the concentration of c-ART-b, which contains the Myc sequence, was based on an ELISA standard curve. Briefly, the microtiter plate was coated with 0.2 μg of a Myc peptide (human c-Myc 408–439) overnight, washed, blocked, and followed by incubation with anti-Myc mAb-HRP conjugates (Invitrogen) in the presence of varying concentrations of the fire Myc peptide for 2 hours. The bound mAb-HRP was detected using a colorimetric substrate tetramethylbenzidine (BioRad). For c-ART-b concentration determination, a c-ART-b sample replaced the free Myc peptide.

EXAMPLE 3

Binding of c-ART-b to MC3R and MC4R

Figure 2:
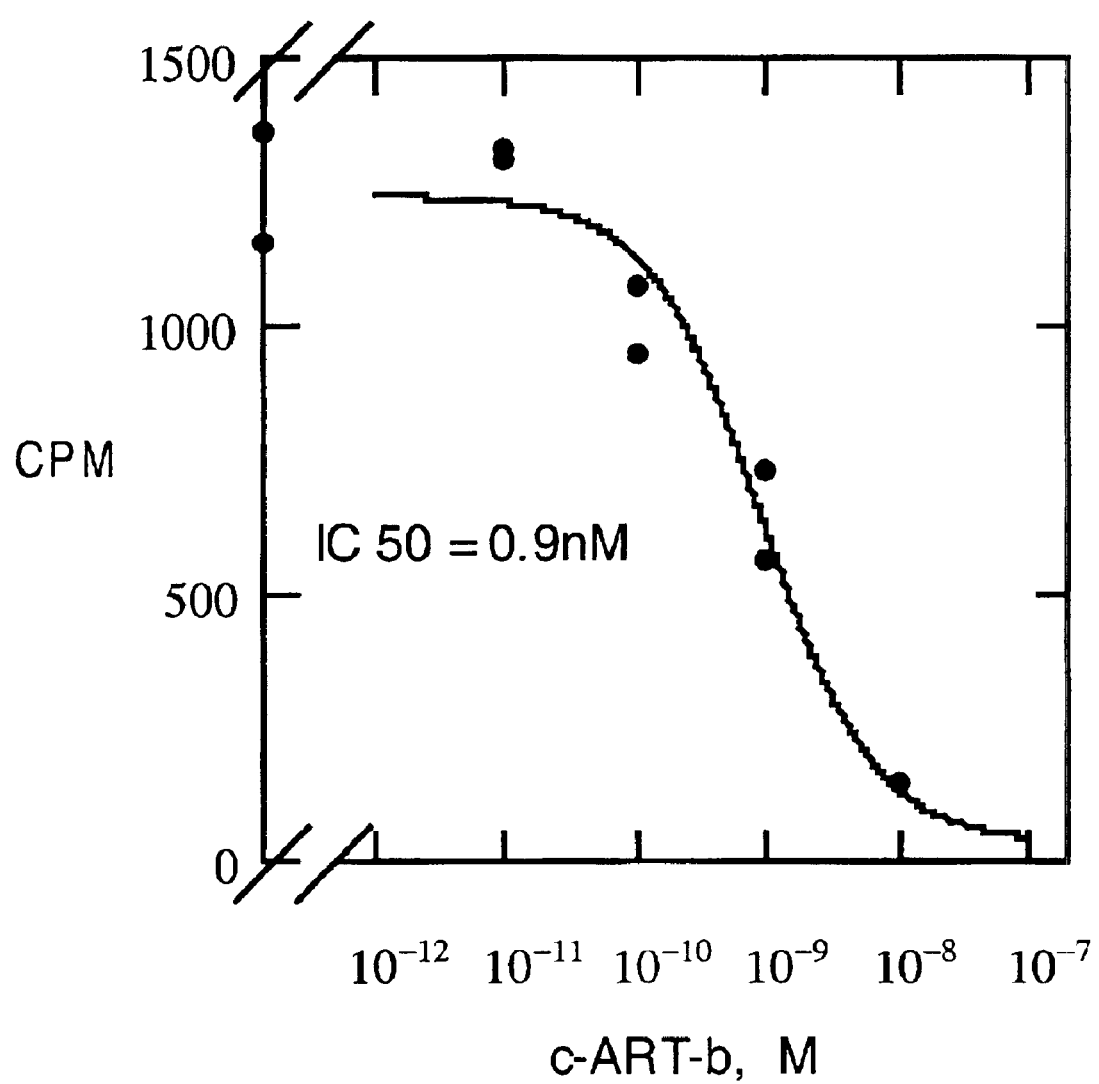
FIG. 2 shows the binding affinity of c-ART-b for the human MC3R. Shown is the inhibition of $^{125}$I-[Tyr$^2$][Nle$^4$, D-Phe$^7$] α-melanocyte stimulating hormone ($^{125}$I-NDP-α-MSH) binding to the human MC3R by c-ART-b.

Binding assays were done in the same manner as described in Fong et al., 1997, Biochem. Biophys. Res. Comm. 237:629–631. Binding assays were carried out using membranes prepared from L cells or CHO cells stably expressing human MC3R, MC4R or MC5R. The binding assay mixture contained 0.2 nM of $^{125}$I-[Tyr$^2$][Nle$^4$, D-Phe$^7$] α-melanocyte stimulating hormone ($^{125}$I-NDP-α-MSH), varying concentrations of c-ART-b or full-length ART protein, and an appropriate amount of membranes so that the total bound radioligand was less than 10% of the added radioligand. The above mixture in binding buffer (50 mM Tris, 2 mM CaCl$_2$, 1 mM MgCl$_2$, 5 mM KCl, pH 7.2) was incubated at room temperature for 2 hours, followed by filtration through GFC paper. The bound ligand was quantitated in a γ counter. IC$_{50}$ values were calculated as previously described (Fong et al., 1996, Mol. Pharmacol. 50:1605–1611). The results are shown in FIG. 2. From FIG. 2 it can be seen that c-ART-b inhibits the binding of $^{125}$I-NDP-α-MSH to MC3R.

Figure 3:
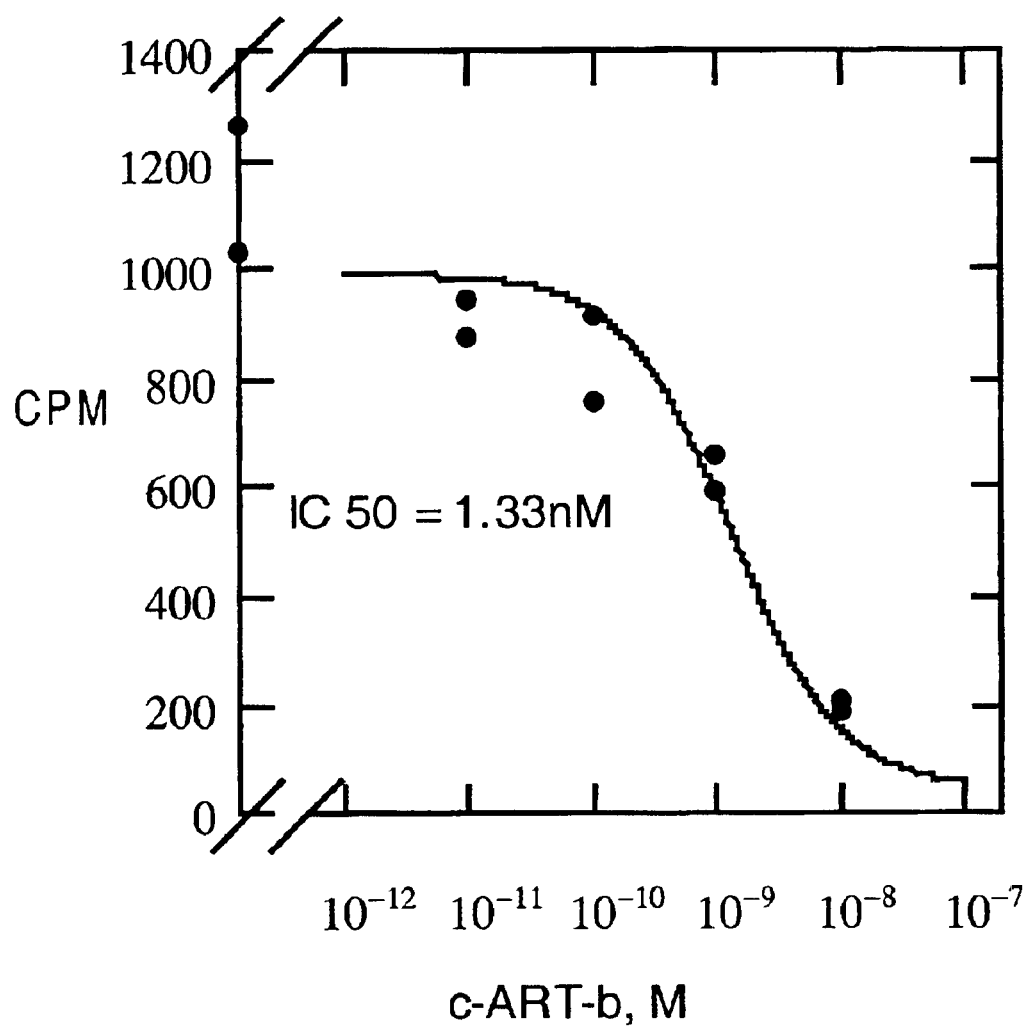
FIG. 3 shows the binding affinity of c-ART-b for the human MC4R. Shown is the inhibition of $^{125}$I-NDP-α-MSH binding to the human MC4R by c-ART-b.

A similar experiment was done to determine whether c-ART-b inhibits the binding of $^{125}$I-labeled NDP-α-MSH to MC4R. The results are shown in FIG. 3. From FIG. 3 it can be seen that c-ART-b inhibits the binding of $^{125}$I-NDP-α-MSH to hMC4R.

Similar experiments were performed with full-length human ART protein. Similar experiments were also performed with full-length ART protein and with c-ART-b for the melanocortin-5 receptor (MC5R). From these experiments, from the results shown in FIGS. 2 and 3, and from similar experiments, the following IC$_{50}$ values for the inhibition of $^{125}$I-labeled NDP-α-MSH to MC3R, MC4R, and MC5R by full-length ART protein and by c-ART-b can be determined.

TABLE 1

|  | hMC3R | hMC4R | hMC5R |
| --- | --- | --- | --- |
| full length ART | 1.0 ± 0.4 (4) | 0.5 ± 0.1 (3) | >40 |
| c-ART-b | 1.9 ± 1.0 (2) | 1.4 ± 0.1 (2) | not done |

The IC$_{50}$ values shown in Table 1 are given in nM. The numbers in parentheses represent the number of experiments run. The results shown in Table 1 indicate that, surprisingly, c-ART-b, although missing a significant amount of sequence from the N-terminus of the ART protein, is essentially functionally equivalent to full length ART protein. In addition, c-ART-b is functional despite having a significant amount of non-ART sequences at its C-terminus (a thrombin site, a myc epitope, and a hexahistidine tag).

EXAMPLE 4
Functional Assay for the Binding of c-ART-b to MC3R and MC4R

The ability of c-ART-b to inhibit the production of cAMP by α-melanocyte stimulating hormone acting through MC3R or MC4R can be demonstrated by preincubating L Cells stably expressing human MC3R or MC4R with c-ART-b for 10 minutes, followed by incubation with 20 nM α-melanocyte stimulating hormone for 45 minutes. The incubation buffer also contains Earle's balanced salt solution, 10 mM HEPES, 5 mM $MgCl_2$, 1 mg/ml BSA and 0.5 mM IBMX. -Following the incubation, cells are lysed by boiling for 4 minutes. Intracellular cAMP concentration is measured by RIA (Huang et al., 1997, J. Receptor Signal Transduc. Res. 17:599–607) using anti-cAMP antibody and $^{125}I$-cAMP as modified in the scintillation proximity assay format (Amersham).

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Various publications are cited herein, the disclosures of which are incorporated by reference in their entireties.

What is claimed is:

1. A fusion protein having an amino acid sequence from the ART protein fused at its carboxy terminus to one or more amino acid sequences not derived from the ART protein, where the amino acid sequence from the ART protein is selected from the group consisting of: SEQ.ID.NOs.:6–8 and 9.

2. The fusion protein of claim 1 having an amino acid sequence selected from the group consisting of: SEQ.ID.NOs.:1–3, 10–12, and 15–16.

3. The fusion protein of claim 2 having the amino acid sequence of SEQ.ID.NO.:2.

4. An ART polypeptide having an amino acid sequence selected from the group consisting of: SEQ.ID.NOs.:6–8 and 9.

5. A DNA sequence encoding the fusion protein of claim 1.

6. A method of determining whether a substance is an inhibitor of the binding of an ART polypeptide to a melanocortin receptor where the method comprises:
   (a) providing cells expressing the melanocortin receptor;
   (b) exposing the cells to a chosen concentration of the melanocyte stimulating hormone in the absence of the ART polypeptide and in the absence of the substance and measuring the amount of melanocyte stimulating hormone binding to the cells to obtain a first value for melanocyte stimulating hormone binding;
   (c) exposing the cells to the chosen concentration of melanocyte stimulating hormone in the presence of a chosen concentration of the ART polypeptide and in the absence of the substance and measuring the amount of melanocyte stimulating hormone binding to obtain a second value for melanocyte stimulating hormone binding where the second value for melanocyte stimulating hormone binding indicates that less melanocyte stimulating hormone binding has occurred as compared to the first value for melanocyte stimulating hormone binding;
   (d) exposing the cells to the chosen concentration of melanocyte stimulating hormone in the presence of the chosen concentration of ART polypeptide and in the presence of the substance and measuring the amount of melanocyte stimulating hormone binding to obtain a third value for melanocyte stimulating hormone binding;
   where, if the third value for melanocyte stimulating hormone binding is greater than the second value, then the substance is an inhibitor of the binding of the ART polypeptide to the melanocortin receptor;
   where the ART polypeptide has an amino acid sequence selected from the group consisting of: SEQ.ID.NOs.:1–3, 6–12, and 15–16.

7. The method of claim 6 where the melanocortin receptor is selected from the group consisting of: the melanocortin-3 receptor (MCR3R) and the melanocortin-4 receptor (MC4R).

8. A method for determining whether a substance is an inhibitor of the binding of an ART polypeptide to a melanocortin receptor where the method comprises:
   (a) providing cells expressing a melanocortin receptor;
   (b) exposing the cells to an ART polypeptide in the presence and in the absence of the substance under conditions such that if the substance were not present, the ART polypeptide would bind to the melanocortin receptor;
   (c) measuring the amount of binding of the ART polypeptide to the melanocortin receptor in the presence and in the absence of the substance;
   where a decrease in the amount of binding of the ART polypeptide to the melanocortin receptor in the presence as compared to the absence of the substance indicates that the substance is an inhibitor of the binding of the ART polypeptide to the melanocortin receptor;
   where the ART polypeptide has an amino acid sequence selected from the group consisting of: SEQ.ID.NOs.:1–3, 6–12, and 15–16.

9. The method of claim 8 where the melanocortin receptor is selected from the group consisting of: the melanocortin-3 receptor (MCR3R) and the melanocortin-4 receptor (MC4R).

10. A method for determining whether a substance is an allosteric enhancer of the binding of an ART polypeptide to a melanocortin receptor where the method comprises:
    (a) providing cells expressing a melanocortin receptor;
    (b) exposing the cells to an ART polypeptide in the presence and in the absence of the substance under conditions such that if the substance were not present, the ART polypeptide would bind to the melanocortin receptor;
    (c) measuring the amount of binding of the ART polypeptide to the melanocortin receptor in the presence and in the absence of the substance;
    where an increase in the amount of binding of the ART polypeptide to the melanocortin receptor in the presence as compared to the absence of the substance indicates that the substance is an allosteric enhancer of the binding of the ART polypeptide to the melanocortin receptor;
    where the ART polypeptide has an amino acid sequence selected from the group consisting of: SEQ.ID.NOs.:1–3, 6–12, and 15–16.

11. The method of claim 10 where the melanocortin receptor is selected from the group consisting of: the melanocortin-3 receptor (MCR3R) and the melanocortin-4 receptor (MC4R).

12. A method for determining whether a substance is a functional inhibitor of the antagonistic effect of an ART polypeptide on a melanocortin receptor where the method comprises:
    (a) providing cells expressing a melanocortin receptor;
    (b) exposing the cells to a melanocyte stimulating hormone selected from the group consisting of: α-melanocyte stimulating hormone, β-melanocyte stimulating hormone, and γ-melanocyte stimulating hormone, in order to activate the melanocortin receptor, leading to the production of cAMP;
    (c) exposing the cells to an ART polypeptide in the presence and in the absence of the substance under conditions such that if the substance were not present, the ART polypeptide would inhibit the production of cAMP mediated by the melanocortin receptor;
    (d) measuring the amount of cAMP produced the presence and in the absence of the substance;
    where an increase in the amount of cAMP produced in the presence as compared to the absence of the substance indicates that the substance is a functional inhibitor of the antagonistic effect of the ART polypeptide on the melanocortin receptor;
    where the ART polypeptide has an amino acid sequence selected from the group consisting of SEQ.ID.NOs.:1–3, 6–12, and 15–6.

13. The method of claim 12 where the melanocortin receptor is selected from the group consisting of: the melanocortin-3 receptor (MCR3R) and the melanocortin-4 receptor (MC4R).

14. A method of determining whether a substance is an inhibitor of the effect of an ART polypeptide comprising:

(a) providing a *Xenopus* melanophore cell line;

(b) exposing the *Xenopus* melanophore cell line to a chosen concentration of α-melanocyte stimulating hormone in the absence of the ART polypeptide and in the absence of the substance and measuring the amount of pigment dispersion to obtain a first value for pigment dispersion;

(c) exposing the *Xenopus* melanophore cell line to the chosen concentration of α-melanocyte stimulating hormone in the presence of the ART polypeptide and in the absence of the substance and measuring the amount of pigment dispersion to obtain a second value for pigment dispersion where the second value for pigment dispersion indicates that less pigment has been dispersed as compared to the first value for pigment dispersion;

(d) exposing the *Xenopus* melanophore cell line to the chosen concentration of α-melanocyte stimulating hormone in the presence of the ART polypeptide and in the presence of the substance and measuring the amount of pigment dispersion to obtain a third value for pigment dispersion;

where if the third value for pigment dispersion indicates that more pigment has been dispersed as compared with the second value, then the substance is an inhibitor of the effect of the ART polypeptide;

where the ART polypeptide has an amino acid sequence selected from the group consisting of: SEQ.ID.NOs.:1–3, 6–12 and 15–16.

15. A method of determining whether a substance is an inhibitor of the binding of an ART polypeptide to a melanocortin receptor comprising:

(a) providing cells expressing the melanocortin receptor;

(b) exposing the cells to a chosen concentration of the melanocyte stimulating hormone and a chosen concentration of the ART polypeptide in the presence and in the absence of the substance and measuring the amount of melanocyte stimulating hormone binding to the cells in the presence and in the absence of the substance;

where an increase in the amount of melanocyte stimulating hormone binding in the presence of the substance indicates that the substance is an inhibitor of the binding of an ART polypeptide to a melanocortin receptor;

where the ART polypeptide has an amino acid sequence selected from the group consisting of: SEQ.ID.NOs.:1–3, 6–12 and 15–16.

16. The method of claim 15 where the melanocortin receptor is selected from the group consisting of: the melanocortin-3 receptor (MCR3R) and the melanocortin-4 receptor (MC4R).

* * * * *